(12) United States Patent
Riccardi et al.

(10) Patent No.: US 12,329,930 B2
(45) Date of Patent: Jun. 17, 2025

(54) SUBARACHNOID FLUID MANAGEMENT METHOD AND SYSTEM

(71) Applicant: EnClear Therapies, Inc., Newburyport, MA (US)

(72) Inventors: Gianna N. Riccardi, South Berwick, ME (US); William X. Siopes, Jr., Lowell, MA (US); Marcie Glicksman, Salem, MA (US); Anthony DePasqua, Newburyport, MA (US); Kevin Kalish, Newburyport, MA (US); Joshua G. Vose, Seattle, WA (US); Rajan Patel, Somerville, MA (US)

(73) Assignee: EnClear Therapies, Inc., Newburyport, MA (US)

( * ) Notice: Subject to any disclaimer, the term of this patent is extended or adjusted under 35 U.S.C. 154(b) by 759 days.

(21) Appl. No.: 17/489,625

(22) Filed: Sep. 29, 2021

(65) Prior Publication Data

US 2022/0096744 A1 Mar. 31, 2022

Related U.S. Application Data

(60) Provisional application No. 63/117,975, filed on Nov. 24, 2020, provisional application No. 63/084,996, filed on Sep. 29, 2020.

(51) Int. Cl.
*A61M 5/168* (2006.01)
*A61M 5/145* (2006.01)
*A61M 5/142* (2006.01)

(52) U.S. Cl.
CPC ........ *A61M 5/16827* (2013.01); *A61M 5/145* (2013.01); *A61M 5/16886* (2013.01);
(Continued)

(58) Field of Classification Search
CPC .. A61M 2202/0464; A61M 2210/0693; A61M 27/006; A61M 5/16827;
(Continued)

(56) References Cited

U.S. PATENT DOCUMENTS 3,929,992 A 12/1975 Sehgal et al.
4,316,885 A 2/1982 Rakhit
(Continued)

FOREIGN PATENT DOCUMENTS

CN 203604173 U 5/2014
CN 106362226 A 2/2017
(Continued)

OTHER PUBLICATIONS

International Search Report and Written Opinion for International Application No. PCT/US2021/052735, mailed Feb. 11, 2022, 28 pages.
(Continued)

*Primary Examiner* — Nilay J Shah
(74) *Attorney, Agent, or Firm* — Nutter McClennen & Fish LLP

(57) ABSTRACT

A CSF management method for use with a patient forms a closed loop CSF circuit between two points on the patient's body. The CSF circuit has a therapeutic inlet to receive a therapeutic material (e.g. a drug), and a pump having a pump outlet to direct CSF along the CSF circuit. The method controls the pump to direct CSF from the pump outlet at a CSF rate that is different from the natural flow rate (i.e., the natural CSF flow rate). The therapeutic material is added to the CSF via the therapeutic input at a therapeutic rate. The CSF rate is different than the therapeutic rate and/or may be greater than the therapeutic rate. Alternative methods may control a bolus drug infusion to localize the application to a target region.

15 Claims, 13 Drawing Sheets

*Method of localizing drug to target area of brain*

(52) U.S. Cl.
CPC ............ *A61M 2005/14208* (2013.01); *A61M 2202/0464* (2013.01); *A61M 2205/3344* (2013.01); *A61M 2205/3389* (2013.01); *A61M 2210/0693* (2013.01)

(58) Field of Classification Search
CPC .... A61M 5/16886; A61M 2005/14208; A61M 2205/3344
See application file for complete search history.

(56) References Cited

U.S. PATENT DOCUMENTS

| | | |
|---|---|---|
| 4,366,241 A | 12/1982 | Tom et al. |
| 4,376,110 A | 3/1983 | David et al. |
| 4,382,445 A | 5/1983 | Sommers |
| 4,517,288 A | 5/1985 | Giegel et al. |
| 4,650,803 A | 3/1987 | Stella et al. |
| 4,655,745 A | 4/1987 | Corbett |
| 4,830,849 A | 5/1989 | Osterholm |
| 4,837,168 A | 6/1989 | de Jaeger et al. |
| 4,950,232 A | 8/1990 | Ruzicka et al. |
| 5,023,263 A | 6/1991 | Von Burg |
| 5,023,264 A | 6/1991 | Caufield et al. |
| 5,100,883 A | 3/1992 | Schiehser |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,162,333 A | 11/1992 | Failli et al. |
| 5,177,203 A | 1/1993 | Failli et al. |
| 5,221,670 A | 6/1993 | Caufield |
| 5,233,036 A | 8/1993 | Hughes |
| 5,256,790 A | 10/1993 | Nelson |
| 5,258,389 A | 11/1993 | Goulet et al. |
| 5,260,300 A | 11/1993 | Hu |
| 5,262,423 A | 11/1993 | Kao |
| 5,302,584 A | 4/1994 | Kao et al. |
| 5,362,718 A | 11/1994 | Skotnicki et al. |
| 5,373,014 A | 12/1994 | Failli et al. |
| 5,378,836 A | 1/1995 | Kao et al. |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,405,316 A | 4/1995 | Magram |
| 5,411,967 A | 5/1995 | Kao et al. |
| 5,434,260 A | 7/1995 | Skotnicki et al. |
| 5,463,048 A | 10/1995 | Skotnicki et al. |
| 5,470,318 A | 11/1995 | Griffith, III et al. |
| 5,480,988 A | 1/1996 | Failli et al. |
| 5,480,989 A | 1/1996 | Kao et al. |
| 5,489,680 A | 2/1996 | Failli et al. |
| 5,491,231 A | 2/1996 | Nelson et al. |
| 5,504,091 A | 4/1996 | Molnar-Kimber et al. |
| 5,531,673 A | 7/1996 | Helenowski |
| 5,563,145 A | 10/1996 | Failli et al. |
| 5,665,772 A | 9/1997 | Cottens et al. |
| 5,780,462 A | 7/1998 | Lee et al. |
| 5,957,912 A | 9/1999 | Heitzmann |
| 6,193,691 B1 | 2/2001 | Beardsley |
| 6,210,346 B1 | 4/2001 | Hall et al. |
| 6,273,913 B1 | 8/2001 | Wright et al. |
| 6,277,983 B1 | 8/2001 | Shaw et al. |
| 6,358,969 B1 | 3/2002 | Shelley et al. |
| 6,471,960 B1 | 10/2002 | Anderson |
| 6,585,764 B2 | 7/2003 | Wright et al. |
| 6,599,275 B1 | 7/2003 | Fischer, Jr. |
| 6,670,168 B1 | 12/2003 | Katz et al. |
| 6,689,085 B1 | 2/2004 | Rubenstein et al. |
| 6,696,488 B2 | 2/2004 | Wolfe et al. |
| 6,808,536 B2 | 10/2004 | Wright et al. |
| 6,916,310 B2 | 7/2005 | Sommerich |
| 7,025,739 B2 | 4/2006 | Saul |
| 7,037,288 B2 | 5/2006 | Rosenberg et al. |
| 7,331,940 B2 | 2/2008 | Sommerich |
| 7,662,140 B2 | 2/2010 | Heruth et al. |
| 7,717,871 B2 | 5/2010 | Odland |
| 7,763,142 B2 | 7/2010 | Watson |
| 7,811,279 B2 | 10/2010 | John |
| 7,887,503 B2 | 2/2011 | Geiger |
| 8,088,091 B2 | 1/2012 | Thomas et al. |
| 8,137,334 B2 | 3/2012 | Heruth et al. |
| 8,206,334 B2 | 6/2012 | Kralick et al. |
| 8,216,173 B2 | 7/2012 | Dacey, Jr. et al. |
| 8,292,856 B2 | 10/2012 | Bertrand et al. |
| 8,435,204 B2 | 5/2013 | Lad et al. |
| 9,097,723 B2 | 8/2015 | Fathollahi et al. |
| 9,138,537 B2 | 9/2015 | Miesel |
| 9,220,424 B2 | 12/2015 | Wilson et al. |
| 9,421,348 B2 | 8/2016 | Lenihan et al. |
| 9,603,792 B2 | 3/2017 | John |
| 9,629,987 B2 | 4/2017 | Anand et al. |
| 9,682,193 B2 | 6/2017 | Anand et al. |
| 9,687,670 B2 | 6/2017 | Dacey, Jr. et al. |
| 9,744,338 B2 | 8/2017 | East et al. |
| 9,770,180 B2 | 9/2017 | Radojicic |
| 9,895,518 B2 | 2/2018 | Lad et al. |
| 9,913,886 B2 | 3/2018 | Kyutoku et al. |
| 9,919,138 B2 | 3/2018 | Lenihan et al. |
| 10,258,781 B2 | 4/2019 | Choi et al. |
| 10,272,188 B1 | 4/2019 | Geiger et al. |
| 10,441,770 B2 | 10/2019 | Singh et al. |
| 10,549,035 B2 | 2/2020 | Hayek |
| 10,653,713 B2 | 5/2020 | Thakker et al. |
| 10,695,484 B1 | 6/2020 | Radojicic |
| 10,864,323 B2 | 12/2020 | Gerrans |
| 10,945,951 B2 | 3/2021 | Verma |
| 11,065,425 B2 | 7/2021 | Lad et al. |
| 11,534,592 B2 | 12/2022 | Singh et al. |
| 2002/0004580 A1 | 1/2002 | Fueyo et al. |
| 2002/0025521 A1 | 2/2002 | Lu et al. |
| 2003/0060436 A1 | 3/2003 | Schneider |
| 2003/0135148 A1 | 7/2003 | Dextradeur et al. |
| 2003/0171738 A1* | 9/2003 | Konieczynski ... A61M 5/14276 604/500 |
| 2004/0068241 A1 | 4/2004 | Fischer |
| 2004/0097814 A1 | 5/2004 | Navakatikyan et al. |
| 2004/0110250 A1 | 6/2004 | Wischik et al. |
| 2004/0138153 A1 | 7/2004 | Ramesh et al. |
| 2004/0185042 A1 | 9/2004 | Scheiflinger et al. |
| 2004/0220510 A1 | 11/2004 | Koullick et al. |
| 2004/0236309 A1 | 11/2004 | Yang |
| 2006/0025726 A1 | 2/2006 | Fischer et al. |
| 2006/0074388 A1 | 4/2006 | Dextradeur et al. |
| 2006/0079740 A1 | 4/2006 | Silver et al. |
| 2006/0264897 A1 | 11/2006 | Lobl et al. |
| 2007/0112293 A1 | 5/2007 | Borgesen |
| 2007/0167867 A1 | 7/2007 | Wolf |
| 2007/0173787 A1 | 7/2007 | Huang et al. |
| 2007/0243179 A1 | 10/2007 | Elia |
| 2008/0082036 A1 | 4/2008 | Trescony et al. |
| 2008/0242590 A1 | 10/2008 | Andersson et al. |
| 2008/0294096 A1 | 11/2008 | Uber, III et al. |
| 2009/0131857 A1 | 5/2009 | Geiger |
| 2010/0030196 A1 | 2/2010 | Hildebrand et al. |
| 2010/0098639 A1 | 4/2010 | Bankiewicz et al. |
| 2010/0234792 A1 | 9/2010 | Dacey, Jr. et al. |
| 2010/0305492 A1 | 12/2010 | Lad et al. |
| 2011/0033463 A1 | 2/2011 | Thakker et al. |
| 2011/0105926 A1 | 5/2011 | Kornet et al. |
| 2012/0238835 A1 | 9/2012 | Hyde et al. |
| 2012/0238936 A1 | 9/2012 | Hyde et al. |
| 2013/0197422 A1 | 8/2013 | Browd et al. |
| 2013/0273203 A1 | 10/2013 | Oestergaard et al. |
| 2014/0018257 A1 | 1/2014 | Suga et al. |
| 2014/0066830 A1 | 3/2014 | Lad et al. |
| 2014/0206102 A1 | 7/2014 | Petrucelli et al. |
| 2014/0276340 A1 | 9/2014 | Ludin et al. |
| 2014/0303455 A1 | 10/2014 | Shachar et al. |
| 2014/0377319 A1 | 12/2014 | Leuthardt et al. |
| 2015/0005800 A1 | 1/2015 | Anile |
| 2015/0094644 A1 | 4/2015 | Lenihan et al. |
| 2015/0201882 A1 | 7/2015 | Swoboda et al. |

(56) References Cited

U.S. PATENT DOCUMENTS

| | | | |
|---|---|---|---|
| 2015/0265171 A1 | 9/2015 | Seaver et al. | |
| 2015/0374898 A1 | 12/2015 | Fujieda et al. | |
| 2016/0002627 A1 | 1/2016 | Bennett et al. | |
| 2016/0025747 A1 | 1/2016 | Ranum et al. | |
| 2016/0051801 A1 | 2/2016 | Vase | |
| 2016/0089521 A1 | 3/2016 | Dragoon et al. | |
| 2016/0183819 A1 | 6/2016 | Burnett et al. | |
| 2016/0361365 A1 | 12/2016 | Lee et al. | |
| 2016/0367166 A1* | 12/2016 | Piron | A61B 5/031 |
| 2017/0059586 A1 | 3/2017 | Petrucelli et al. | |
| 2017/0095649 A1* | 4/2017 | Vase | A61M 27/006 |
| 2017/0137492 A1 | 5/2017 | Looby | |
| 2017/0157038 A1 | 6/2017 | Peyman | |
| 2017/0157374 A1 | 6/2017 | Hedstrom et al. | |
| 2017/0203084 A1 | 7/2017 | Lad et al. | |
| 2017/0313687 A1 | 11/2017 | Hendrickson et al. | |
| 2018/0028746 A1 | 2/2018 | Abrams et al. | |
| 2018/0185058 A1 | 7/2018 | Anand et al. | |
| 2018/0371010 A1 | 12/2018 | Vassylyev et al. | |
| 2019/0009014 A1 | 1/2019 | Chen et al. | |
| 2019/0048371 A1 | 2/2019 | Basheer et al. | |
| 2019/0083303 A1 | 3/2019 | Khanna | |
| 2019/0085336 A1 | 3/2019 | Zhu et al. | |
| 2019/0089521 A1 | 3/2019 | Coulthard et al. | |
| 2019/0160254 A1 | 5/2019 | Anand et al. | |
| 2019/0290481 A1 | 9/2019 | Martinez et al. | |
| 2019/0317099 A1 | 10/2019 | Halbert et al. | |
| 2020/0001059 A1 | 1/2020 | Campbell et al. | |
| 2020/0046952 A1 | 2/2020 | Vase | |
| 2020/0046953 A1 | 2/2020 | Vase | |
| 2020/0046954 A1 | 2/2020 | Lad et al. | |
| 2020/0118676 A1 | 4/2020 | Spohn et al. | |
| 2020/0324006 A1 | 10/2020 | Paul et al. | |
| 2020/0330497 A1 | 10/2020 | Marcotulli et al. | |
| 2021/0023293 A1 | 1/2021 | DePasqua et al. | |
| 2021/0033620 A1 | 2/2021 | Porter et al. | |
| 2021/0046473 A1 | 2/2021 | Needham et al. | |
| 2021/0077016 A1 | 3/2021 | Bodner | |
| 2021/0145944 A1 | 5/2021 | Navia et al. | |
| 2021/0154276 A1 | 5/2021 | Navia et al. | |
| 2021/0162173 A1 | 6/2021 | Singh et al. | |
| 2021/0369941 A1 | 12/2021 | Korshøj et al. | |
| 2021/0379344 A1 | 12/2021 | Hakim | |
| 2022/0096743 A1 | 3/2022 | Riccardi et al. | |
| 2022/0096745 A1 | 3/2022 | Riccardi et al. | |
| 2022/0105322 A1 | 4/2022 | Riccardi et al. | |
| 2022/0134076 A1 | 5/2022 | Bodner | |
| 2022/0160947 A1 | 5/2022 | DePasqua et al. | |
| 2022/0257854 A1 | 8/2022 | Bodner et al. | |
| 2022/0313890 A1 | 10/2022 | Riccardi et al. | |
| 2022/0355015 A1 | 11/2022 | Patel et al. | |
| 2022/0370716 A1 | 11/2022 | Martin et al. | |
| 2022/0379010 A1 | 12/2022 | Martin et al. | |
| 2022/0401645 A1 | 12/2022 | Morse et al. | |
| 2023/0001165 A1 | 1/2023 | Bourouiba et al. | |
| 2023/0056486 A1 | 2/2023 | Navia et al. | |
| 2023/0321412 A1 | 10/2023 | Tseng et al. | |
| 2023/0355118 A1 | 11/2023 | Patel et al. | |
| 2024/0285854 A1 | 8/2024 | Glicksman et al. | |

FOREIGN PATENT DOCUMENTS

| | | | |
|---|---|---|---|
| EP | 1481697 A1 | 12/2004 | |
| EP | 1731182 A1 | 12/2006 | |
| EP | 3294398 A1 | 3/2018 | |
| EP | 3833251 A1 | 6/2021 | |
| EP | 4030988 A1 | 7/2022 | |
| JP | 2002/136295 A | 5/2002 | |
| WO | 98/02441 A2 | 1/1998 | |
| WO | 99/13886 A1 | 3/1999 | |
| WO | 99/15530 A1 | 4/1999 | |
| WO | 2000/056335 A1 | 9/2000 | |
| WO | 01/14387 A1 | 3/2001 | |
| WO | 2001/039819 A2 | 6/2001 | |
| WO | 2003015710 A2 | 2/2003 | |
| WO | WO-03015710 A2 * | 2/2003 | A61K 38/48 |
| WO | 03/057218 A1 | 7/2003 | |
| WO | 2003/015710 A3 | 2/2004 | |
| WO | 2004/058337 A1 | 7/2004 | |
| WO | 2004/091444 A2 | 10/2004 | |
| WO | 2008/105959 A2 | 9/2008 | |
| WO | WO-2008140546 A2 * | 11/2008 | A61F 9/0008 |
| WO | 2010123558 A1 | 10/2010 | |
| WO | 2011114260 A1 | 9/2011 | |
| WO | 2014/159247 A1 | 10/2014 | |
| WO | 2014/159757 A2 | 10/2014 | |
| WO | 2015/049588 A2 | 4/2015 | |
| WO | 2014/124365 A3 | 10/2015 | |
| WO | 2016/143227 A1 | 9/2016 | |
| WO | 2016183123 A1 | 11/2016 | |
| WO | 2017/078695 A1 | 5/2017 | |
| WO | 2017096228 A1 | 6/2017 | |
| WO | 2018005621 A1 | 1/2018 | |
| WO | 2018/160993 A1 | 9/2018 | |
| WO | 2019/028006 A1 | 2/2019 | |
| WO | 2019/100074 A1 | 5/2019 | |
| WO | 2020/010074 A1 | 1/2020 | |
| WO | 2020/023417 A1 | 1/2020 | |
| WO | 2020/023418 A1 | 1/2020 | |
| WO | 2020/033773 A1 | 2/2020 | |
| WO | 2020064875 A1 | 4/2020 | |
| WO | 2020/149993 A1 | 7/2020 | |
| WO | 2020/210634 A1 | 10/2020 | |
| WO | 2021/055100 A1 | 3/2021 | |
| WO | 2022/076598 A1 | 4/2022 | |
| WO | 2022/173620 A1 | 8/2022 | |
| WO | 2022/246042 A1 | 11/2022 | |

OTHER PUBLICATIONS

Abbott, N., et al., "The role of brain barriers in fluid movement in the CNS: is there a 'glymphatic' system?" Acta Neuropathologica vol. 135, 2018, pp. 387-407.

Allen, J., et al., "Abstract 3483: Modeling circulating tumor cells in the peripheral blood and CSF of breast cancer patients," Cancer Research vol. 73, Issue 8, 2013, abstract only.

Allen, J., et al., "Abstract 5565: Circulating tumor cells in the peripheral blood and cerebrospinal fluid of patients with central nervous system metastases," Cancer Research vol. 72, Issue 8, 2012, abstract only.

Andersen, P., et al., "Clinical genetics of amyotrophic lateral sclerosis: what do we really know?" Nature Reviews Neurology, vol. 7, 2011, pp. 603-615.

Arai, T., et al., "Phosphorylated and cleaved TDP?43 in ALS, FTLD and other neurodegenerative disorders and in cellular models of TDP?43 proteinopathy," Neuropathology, vol. 30, 2010, pp. 170-181.

Arai, T., et al., "TDP-43 is a component of ubiquitin-positive tau-negative inclusions in frontotemporal lobar degeneration and amyotrophic lateral sclerosis," Biochemical and Biophysical Research Communications, vol. 351, Issue 3, 2006, pp. 602-611.

Arriagada, P., et al., "Neurofibrillary tangles but not senile plaques parallel duration and severity of Alzheimer's disease," Neurology 42, 1992, pp. 631-639.

Asai, D., et al., "Chapter 3 Making Monoclonal Antibodies," Methods in Cell Biology, vol. 37, 1993, pp. 57-74.

Bioline "Proteinase K" accessed from bioline.com on Jun. 22, 2021 (Year: 2013).

Brat, D., et al., "Tau?associated neuropathology in ganglion cell tumours increases with patient age but appears unrelated to ApoE genotype," Neuropathy and Applied Neurobiology, vol. 27, Issue 3, 2001, pp. 197-205.

Buee, L., et al., "Tau protein isoforms, phosphorylation and role in neurodegenerative disorders," Brain Research Reviews, vol. 33, Issue 1, 2000, pp. 95-130.

Chang, Y., et al., "The Glycine-Alanine Dipeptide Repeat from C9orf72 Hexanucleotide Expansions Forms Toxic Amyloids Possessing Cell-to-Cell Transmission Properties" Journal of Biological Chemistry, vol. 291, Issue 10, 2016, pp. 4903-4911.

(56) References Cited

OTHER PUBLICATIONS

Coatti, G., et al., "Pericytes Extended Survival of ALS SOD1 Mice and Induce the Expression of Antioxidant Enzymes in the Murine Model and in IPSCs Dervised Neuronal Cells from an ALS Patient," Stem Cell Reviews and Reports (2017) 13: 686-698.

De Souza, P., et al., "A biotechnology perspective of fungal proteases," Brazilian Journal of Microbiology, vol. 46, 2, 2015, pp. 337-346.

Dejesus-Hernandez, M., et al., "Expanded GGGGCC Hexanucleotide Repeat in Noncoding Region of C9ORF72 Causes Chromosome 9p-Linked FTD and ALS," Neuron, vol. 72, 2011, pp. 245-256.

Diamond, S., "Methods for mapping protease specificity," Current Opinion in Chemical Biology, vol. 11, Issue 1, 2007, pp. 46-51.

Evidente, V., et al., "Post-encephalitic parkinsonism," Journal of Neurology, Neurosurgery & Psychiatry, vol. 63, Issue 1, 1998, pp. 5.

Extended European Search Report for European Application No. 19839881.0 dated Jun. 21, 2022, 9 pages.

Extended European Search Report for European Application No. 19840444.4 dated Jun. 28, 2022, 7 pages.

Finsterer, J., et al., "Liquorpheresis (CSF filtration) in familial amyotrophic lateral sclerosis," Spinal Cord, vol. 39, 1999, pp. 592-593.

Giannakopoulos, P., et al., Tangle and neuron numbers, but not amyloid load, predict cognitive status in Alzheimer's disease, Neurology, vol. 60, 2003, pp. 1495-1500.

Giordana, M., et al., "Dementia and cognitive impairment in amyotrophic lateral sclerosis: a review," Neurological Sciences, vol. 32, 2011, pp. 9-16.

Gomez-Isla, T., et al., Neuronal loss correlates with but exceeds neurofibrillary tangles in Alzheimer's disease, Annals of Neurology, vol. 41, 1997, pp. 17-24.

Grad, L., et al., "Prion-like activity of Cu/Zn superoxide dismutase: implications for amyotrophic lateral sclerosis," 8:1, 2014, pp. 33-41.

Graff-Radford, N., et al., "Frontotemporal dementia," Seminars in Neurology vol. 27, 2007, pp. 48-57.

Hasegawa, M., et al., "Molecular Dissection of TDP-43 Proteinopathies," Journal of Molecular Neuroscience, vol. 45, 2011, pp. 480-485.

Hasegawa, M., et al., "Phosphorylated TDP-43 in frontotemporal lobar degeneration and amyotrophic lateral sclerosis," Annals of Neurology, vol. 62, Issue 1, 2008, pp. 60-70.

Hersh, D., et al., "MR-guided transcranial focused ultrasound safely enhances interstitial dispersion of large polymeric nanoparticles in the living brain," PLOS One 13(2): e0192240, 2018, 19 pages.

Indivero, V., "Technique filters cancer where chemo can't reach: A new therapy may help cancer patients with malignant ce4lls near the spinal cord and in the brain," dated Jul. 30, 2013. Retrieved from the internet under https://news.psu.edu/story/282970/2013/07/30/research/technique-filters-cancer-where-chemo-cant-reach, 4 pages.

International Preliminary Report on Patentability for International Application No. PCT/US2019/042880, mailed Jan. 12, 2021 (8 pages).

International Preliminary Report on Patentability for International Application No. PCT/US2020/027683, mailed Oct. 21, 2021 (11 pages).

International Search Report and Written Opinion for International Application No. PCT/US2019/042879, mailed Oct. 8, 2019 (14 pages).

International Search Report and Written Opinion for International Application No. PCT/US2019/042880, mailed Oct. 16, 2019 (10 pages).

International Search Report and Written Opinion for International Application No. PCT/US2020/027683, mailed Aug. 6, 2020 (19 pages).

International Search Report and Written Opinion for International Application No. PCT/US2021/013458, mailed Jun. 9, 2021 (20 pages).

International Searching Authority, International Search Report for International Application No. PCT/US2021/053829, dated mailed Jan. 13, 2022, together with the Written Opinion of the International Searching Authority, 19 pages.

International Searching Authority, International Search Report for International Application No. PCT/US2022/037609, dated Oct. 26, 2022, together with the Written Opinion of the International Searching Authority, 8 pages.

International Searching Authority, International Search Report for International Application No. PCT/US22/34706, dated Oct. 18, 2022, together with the Written Opinion of the International Searching Authority, 8 pages.

Jessen, N., et al., "The Glymphatic System—A Beginner's Guide," Neurochemical Research, 2015, 40(2), pp. 2583-2599.

Kaufman, S., et al., "Prion-Like Propagatio of Protein Aggregation and Related Therapeutic Strategies," Neurotherapeutics, 10, 2013, pp. 371-382.

Kim Kwang Soo, et al., "Proteolytic Cleavage of Extracellular a-Synuclein by Plasmin: Implications for Parkinson Disease" Journal of Biological Chemistry, vol. 287, No. 30, Mar. 22, 2012, pp. 24862-24872.

Kopeikina, K., et al., "Soluble forms of tau are toxic in Alzheimer's disease," Translational Neuroscience 3(3), 2012, pp. 223-233.

Kouzehgarani, G., et al., "Harnessing cerebrospinal fluid circulation for drug delivery to brain tissues, Advanced Drug Delivery Reviews," 2021, vol. 173, pp. 20-59.

Lee, V., et al., "Neurodegenerative tauopathies," Annual Review of Neuroscience, vol. 24, 2001, pp. 1121-1159.

Legon, W., et al., "Transcranial focused ultrasound modulates the activity of primary somatosensory cortex in humans," Nature Neuroscience vol. 17, No. 2, 2014, pp. 322-329.

Lei, P., et al., "Tau protein: relevance to Parkinson's disease," The International Journal of Biochemistry & Cell Biology, vol. 42, Issue 11, 2010, pp. 1775-1778.

Lin, Z., et al., "Facile synthesis of enzyme—inorganic hybrid nanoflowers and their application as an immobilized trypsin reactor for highly efficient protein digestion." (Communication) RSC Adv., 2014, 4, 13888-13891.

Lipsman, N., et al., "Blood-brain barrier opening in Alzheimer's disease using MR-guided focused ultrasound," Nature Communications vol. 9, Article 2336, 2018, pp. 1-8.

Lomen-Hoerth, C., et al., "The overlap of amyotrophic lateral sclerosis and frontotemporal dementia," Neurology, vol. 59, 2002, pp. 1077-1079.

Marx, S., et al., "Bench to Bedside: The Development of Rapamycin and Its Application to Stent Restenosis", Journal of the American Heart Association 104, 2001, pp. 852-855.

May, S., et al., "C9orf72 FTLD/ALS-associated Gly-Ala dipeptide repeat proteins cause neuronal toxicity and Unc119 sequestration," Acta Neuropathologica, vol. 128, 2014, pp. 485-503.

Mckee, A., et al., "The Neuropathology of Chronic Traumatic Encephalopathy," Brain Pathology 253), 2015, pp. 350-364.

Mcrae et al., Mapping the active sites of bovine thrombin, factor IXa, factor Xa, factor XIa, factor XIIa, plasma kallikrein, and trypsin with amino acid and peptide thioesters: development of new sensitive substrates. Biochemistry 1981, 20, 25, pp. 7196-7206.

Menendez-Gonzalez, M., et al., "Targeting Beta-Amyloid at the CSF: A New Therapeutic Strategy in Alzheimer's Disease," Frontiers in Aging Neuroscience, vol. 10, 2018, pp. 1-8.

Mori, K., et al., "The C9orf72 GGGGCC repeat is translated into aggregating dipeptide-repeat proteins in FTLD/ALS," Science, vol. 339, No. 6125, Feb. 7, 2013, pp. 1335-1338.

Narasimhan, S., et al., "Pathological Tau Strains from Human Brains Recapitulate the Diversity of Tauopathies in Nontransgenic Mouse Brain," The Jorunal of Neuroscience, vol. 37, Issue 47, 2017, pp. 11406-11423.

Neumann, M., et al., "Ubiquitinated TDP-43 in frontotemporal lobar degeneration and amyotrophic lateral sclerosis," Science, vol. 314, 2006, pp. 130-133.

Ohki, Y., et al., "Glycine-alanine dipeptide repeat protein contributes to toxicity in a zebrafish model of C9orf72 associated neurodegeneration," Molecular Neurodegeneration (2017) 12:6, pp. 1-11.

(56) References Cited

OTHER PUBLICATIONS

Ozcelik, A., et al., "Acoustic tweezers for the life sciences," Nature Methods vol. 15, 2018, pp. 1021-1028.
Paraskevas, G., et al., "The emerging TDP-43 proteinpathy" Neuroimmunol Neuroinflammation 5:17 (Year 2018).
Pardridge, W., et al., "CSF, blood-brain barrier, and brain drug delivery," Expert Opinion on Drug Delivery, vol. 13, 2016, pp. 1-13.
Patel, A., et al., "Identification and enumeration of circulating tumor cells in the cerebrospinal fluid of breast cancer patents with central nervous system metastases," Oncotarget, vol. 2, No. 10, 2011, pp. 752-760.
Poreba, M., et al., "Current Strategies for Probing Substrate Specificity of Proteases," Current Medicinal Chemistry, vol. 17, Issue 33, 2010, pp. 3968-3995.
Quinn, J., et al., "Tau Proteolysis in the Pathogenesis of Tauopathies: Neurotoxic Fragments and Novel Biomarkers," Journal of Alzheimer's Disease, vol. 63, No. 1, 2018, pp. 13-33.
Reinhard, M., et al., "Blood-Brain Barrier Disruption By Low-Frequency Ultrasound," Stroke, vol. 37, 2006, pp. 1546-1548.
Saido, T., et al., "Proteolytic Degradation of Amyloid 13-Protein" Cold Spring Harbor Perspectives in Medicine, vol. 2, No. 6, Jun. 1, 2012, pp. a006379-a006379.
Sonabend, A., et al., "Overcoming the Blood-Brain Barrier with an Implantable Ultrasound Device," Clinical Cancer Research, vol. 25, Issue 13, 2019, pp. 3750-3752.
Song, J., et al., "Investigation of standing wave formation in a human skull for a clinical prototype of a large-aperture, transcranial MR-guided Focused Ultrasound (MRgFUS) phased array: An experimental and simulation study," IEEE Transactions on Biomedical Engineering, vol. 59, Issue 2, 2012, pp. 435-444.
Spencer, B., et al., "Lentivirus Mediated Delivery of Neurosin Promotes Clearance of Wild-type a-Synuclein and Reduces the Pathology in an a-Synuclein Model of LBD", Molecular Therapy, vol. 21, No. 1, Jan. 1, 2013, pp. 31-41.
Steele, J., et al., "Progressive Supranuclear Palsy A Heterogeneous Degeneration Involving the Brain Stem, Basal Ganglia and Cerebellum With Vertical Gaze and Pseudobulbar Palsy, Nuchal Dystonia and Dementia," Arch Neurol. vol. 10, No. 4, 1964, pp. 333-359.
Takalo, M., et al., "Protein aggregation and degradation mechanisms in neurodegenerative diseases," American Journal of Neurodegenerative Disease, 2013; 2(1), pp. 1-14.
Tanji, K., et al., "Proteinase K-resistant a-synuclein is deposited in presynapses in human Lewy body disease and A53T a-synuclein transgenic mice," Acta Neuropathologica, Springer, Berlin, DE, vol. 120, No. 2, Mar. 26, 2010, pp. 145-154.
Tarasoff-Conway, J., et al., "Clearance systems in the brain implications for Alzheimer disease," Nature Reviews Neurology 11(8), 2015, pp. 457-470.
Tyler, W., et al., "Remote Excitation of Neuronal Circuits Using Low-Intensity, Low-Frequency, Ultrasound," PLOS One vol. 3, Issue 10, 2008, e3511, 11 pages.
Westergard, T., et al., "Cell-to-Cell Transmission of Dipeptide Repeat Proteins Linked to C9orf72-ALS/FTD," Cell Reports, vol. 17, Issue 3, 2016, pp. 645-652.
Wray, S., et al., "Direct analysis of tau from PSP brain identifies new phosphorylation sites and a major fragment of N?terminally cleaved tau containing four microtubule?binding repeats," Journal of Neurochemistry, vol. 105, 2008, pp. 2343-2352.
Written Opinion of the International Preliminary Examining Authority for International Application No. PCT/US2019/042879, mailed Feb. 25, 2021 (6 pages).
Written Opinion of the International Preliminary Examining Authority for International Application No. PCT/US2019/042880, mailed Sep. 11, 2020 (8 pages).
Wszolek, Z., et al., "Frontotemporal dementia and parkinsonism linked to chromosome 17 (FTDP-17)" Orphanet Journal of Rare Diseases, 2006, 1:30, pp. 1-9.
Xie, L., et al., "Sleep Drives Metabolite Clearance from the Adult Brain," Science vol. 342, Issue 6156, 2013, pp. 373-377.
Zhang, Y., et al., "Aggregation-prone c9FTD/ALS poly(GA) RAN-translated proteins cause neurotoxicity by inducing ER stress," Acta Neuropathologica, vol. 128, 2014, pp. 504-524.
Extended European Search Report for application No. PCT/US2021052735 dated Oct. 8, 2024 (18 pages).
Chinese Office Action for Chinese Application No. 202080041867.5, dated Jul. 12, 2023 (12 pages).
International Search Report and Written Opinion for International Application No. PCT/US23/17893, mailed Jun. 29, 2023 (13 pages).
International Searching Authority, International Search Report for International Application No. PCT/US2024/017736, dated Aug. 19, 2024, together with the Written Opinion of the International Searching Authority, 15 pages.
International Search Report and Written Opinion for International Application No. PCT/US2023/015972, mailed Jul. 27, 2023, 12 pages.
First Chinese Office Action for Chinese Patent Application No. 202080041867.5, with English translation, dated Jul. 12, 2023 (24 pages).
Notice of Reasons for Refusal for Japanese Patent Application No. 2021-560113, with English translation, dated Jan. 4, 2024 (12 pages).
Second Chinese Office Action for Chinese Patent Application No. 202080041867.5, with English translation, dated Apr. 30, 2024 (26 pages).
Extended European Search Report for European Patent Application No. 20788080.8, dated Jun. 4, 2024 (12 pages).
Non-Final Office Action for U.S. Appl. No. 17/489,633 dated May 29, 2024 (8 pages).
Office Action Decision of Refusal from Japanese Patent Office for application No. 2021-560113 dated Jun. 25, 2024, 5 pages.
International Search Report and Written Opinion for PCT/2024/017736 dated Aug. 19, 2024, 15 pages.

* cited by examiner

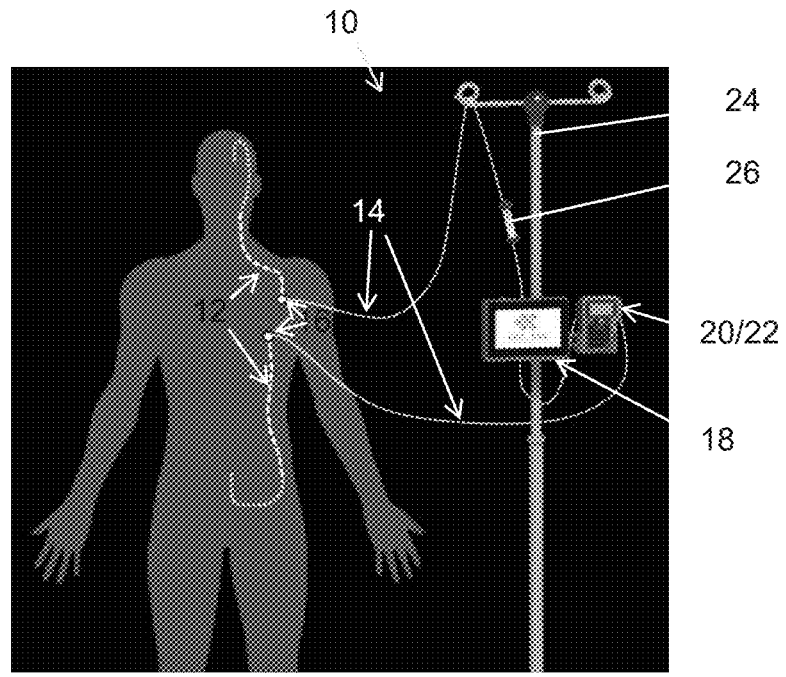
*Figure 1A: CSF Circuit*
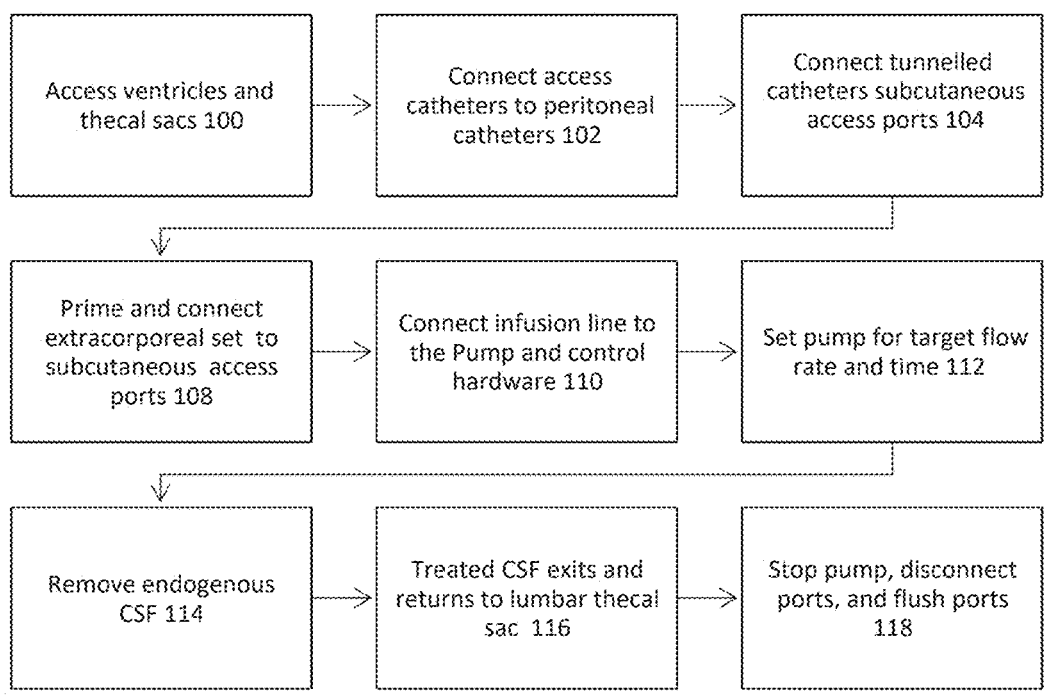
*Figure 1C: High-level surgical flow*

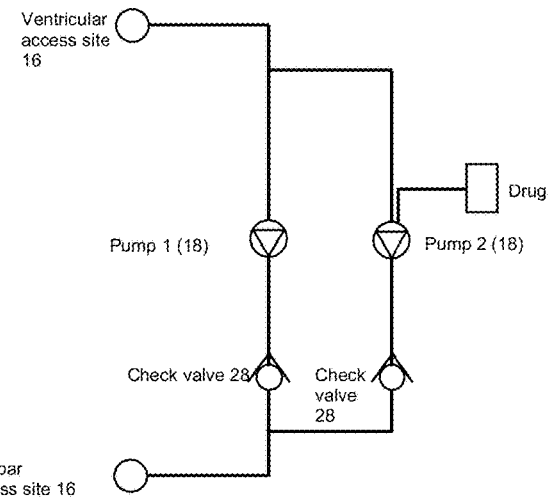
*Figure 2. Two pump circuit with drug fed into pump through separate fluid line*
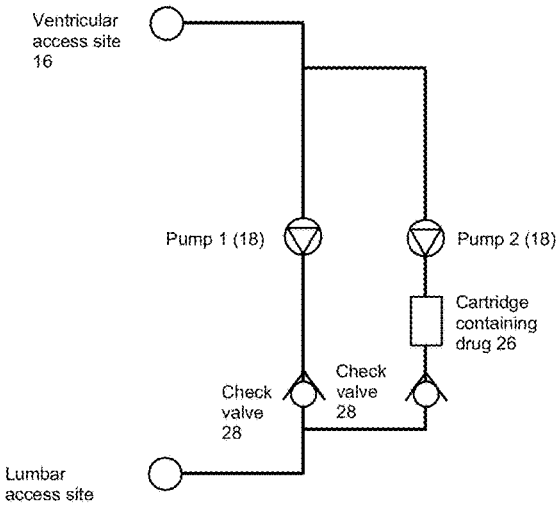
*Figure 3: Two pump circuit with drug introduced directly into fluid line*
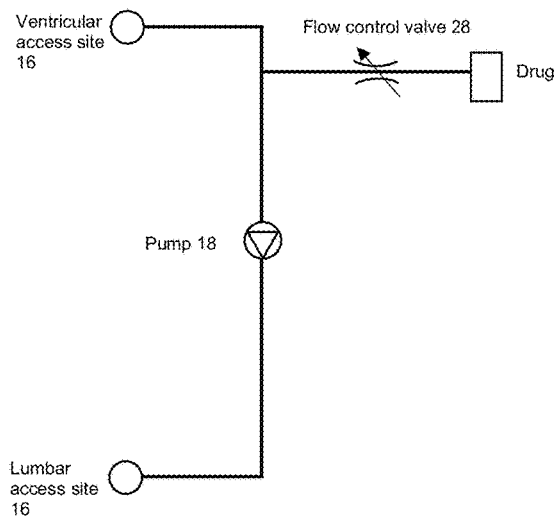
*Figure 4A: Flow control valve circuit*

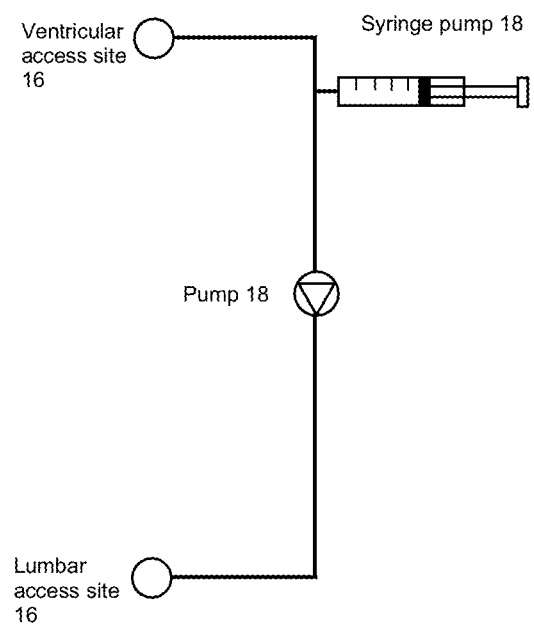
*Figure 4b: Syringe pump dosing circuit*

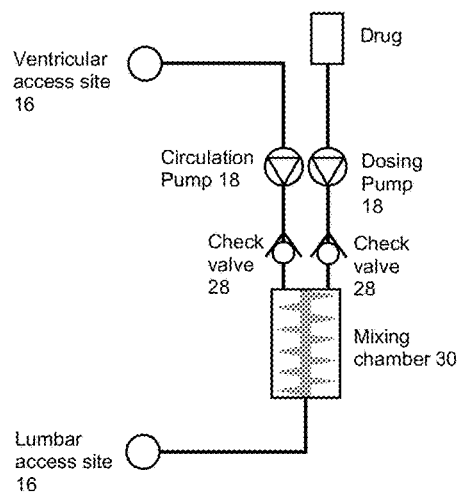
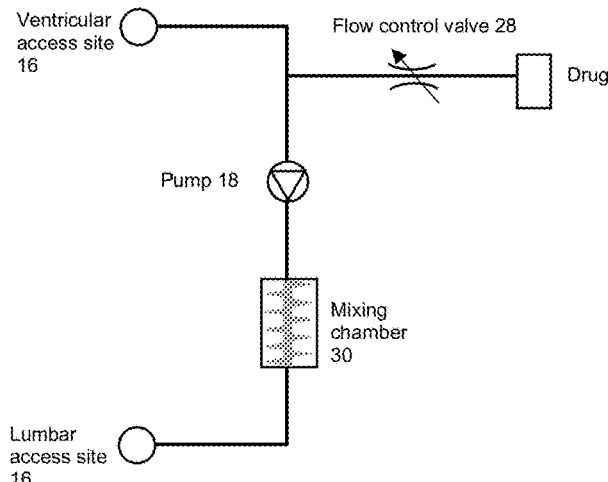
*Figure 5: Two-pump circuit with mixing chamber*   *Figure 6: Flow control valve circuit with mixing chamber*
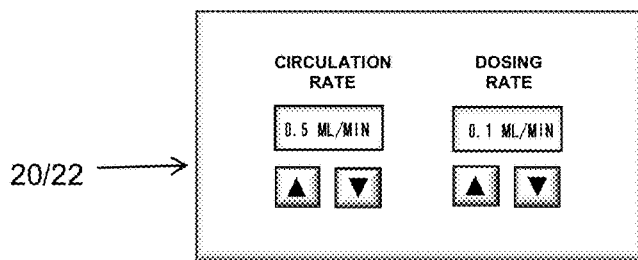
*Figure 7: System interface with controls for circulation rate of CSF and dosing rate of drug*
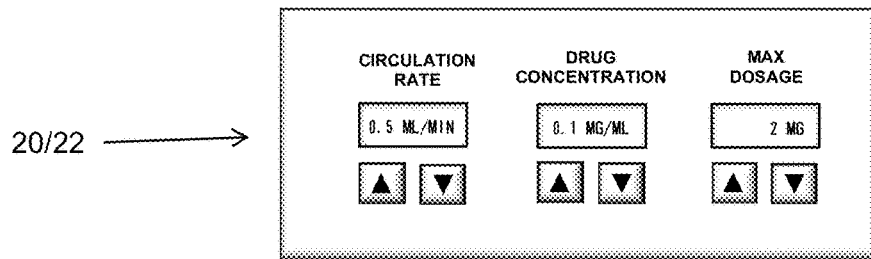
*Figure 8: System interface with controls for circulation rate of CSF, target drug concentration in CSF, and max dosage of drug*

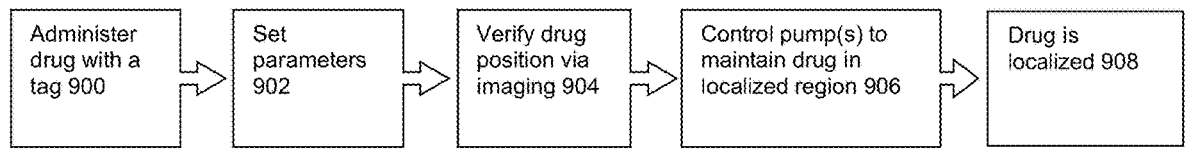
*Figure 9: Method of localizing drug to target area of brain*
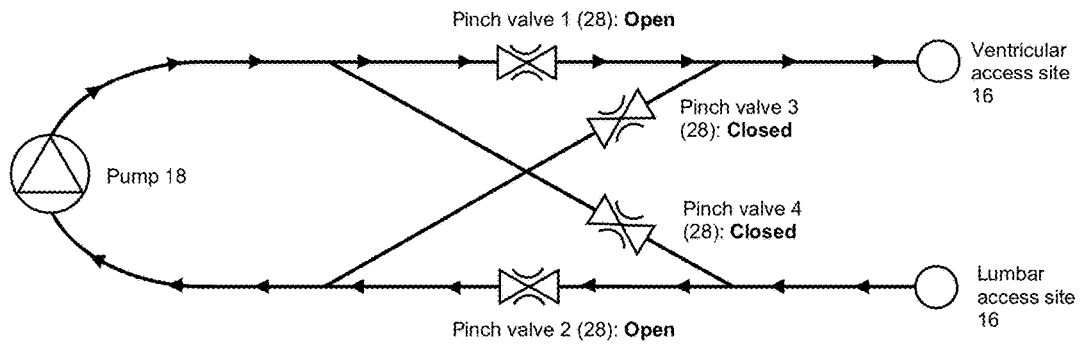
*Figure 10: Directing flow from lumbar to ventricle*
To direct flow from ventricle to lumbar:
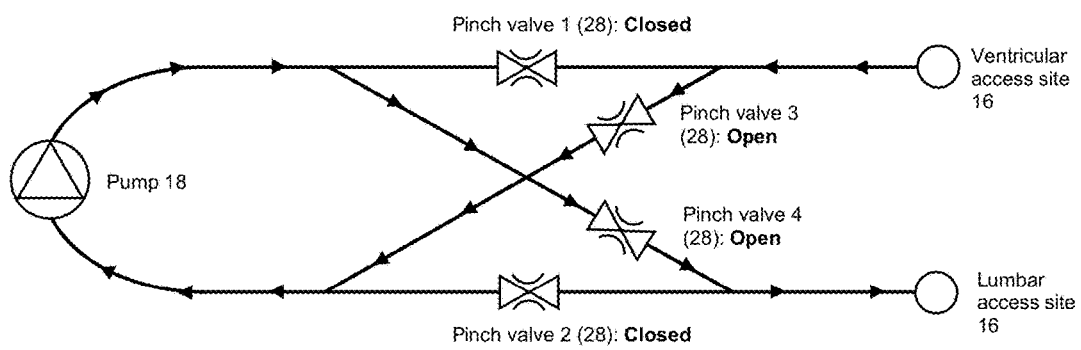
*Figure 11: Directing flow from ventricle to lumbar*

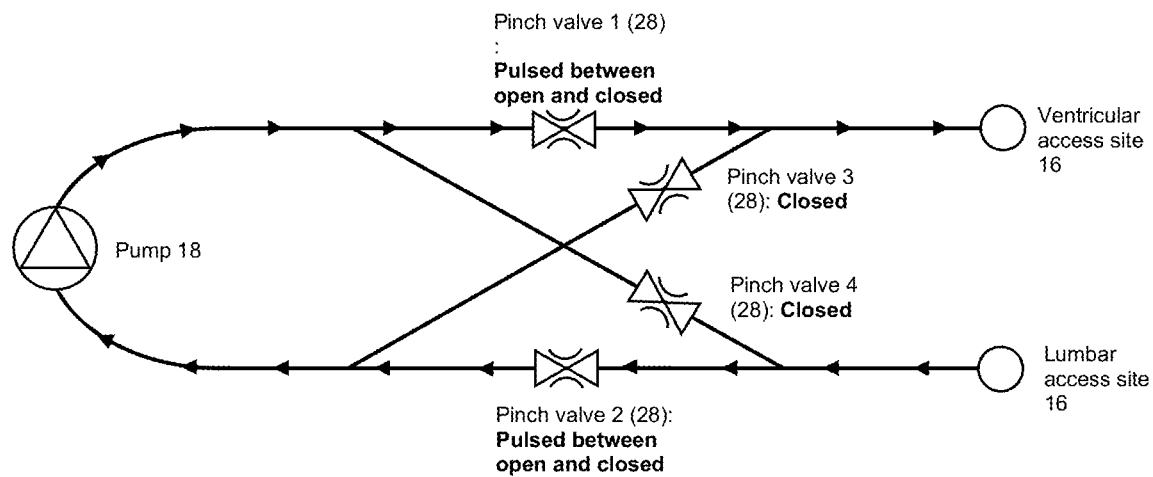
*Figure 12: Flowing from lumbar to ventricle with a pulsatile flow pattern*
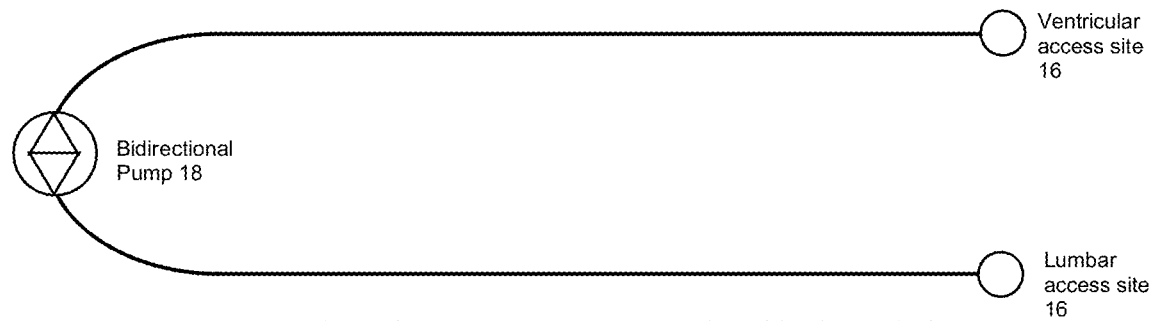
*Figure 13A: Bidirectional pump circuit which enables flow in both directions*

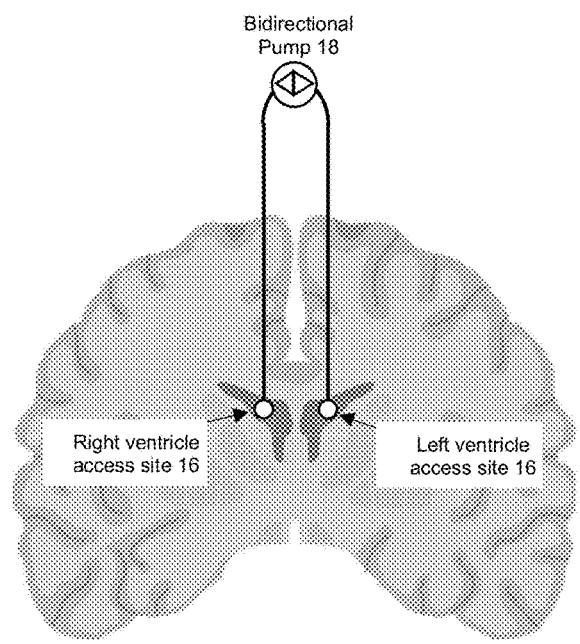
Figure 13B: Bidirectional pump circuit which enables flow in both directions between right and left ventricles in the brain
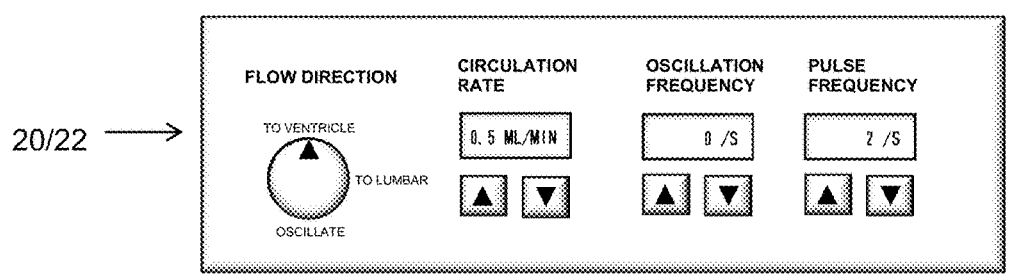
Figure 14: System interface with controls for flow direction of CSF, circulation rate, frequency of oscillations between flow directions, and pulse frequency

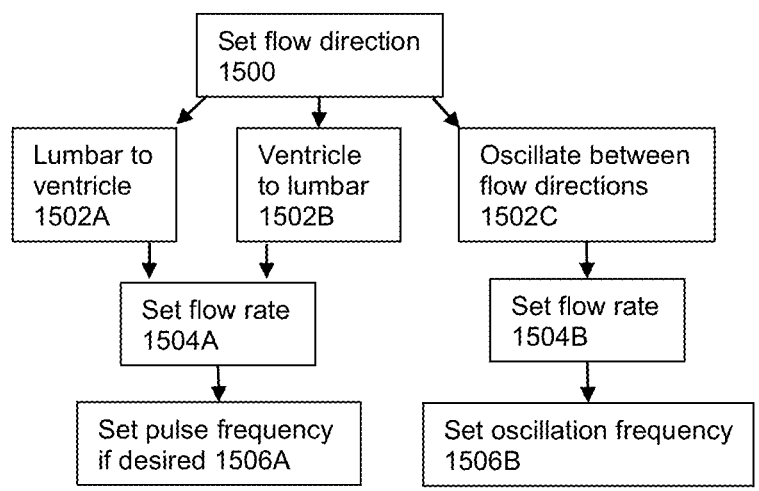
Figure 15: Method to manually program method of delivery

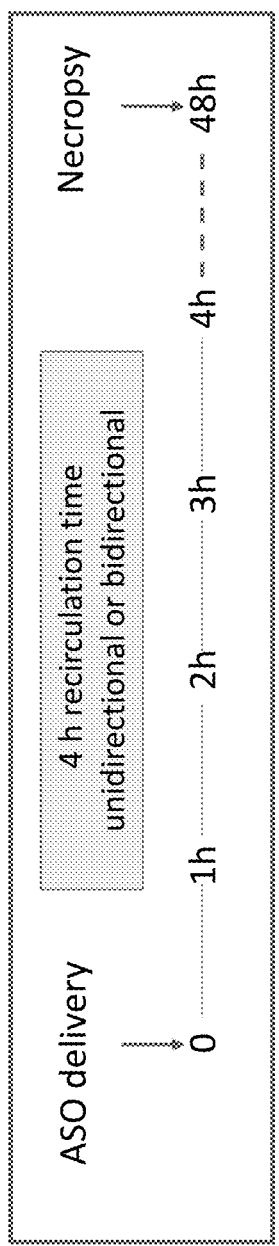
Figure 17A: Schema of in-vivo study
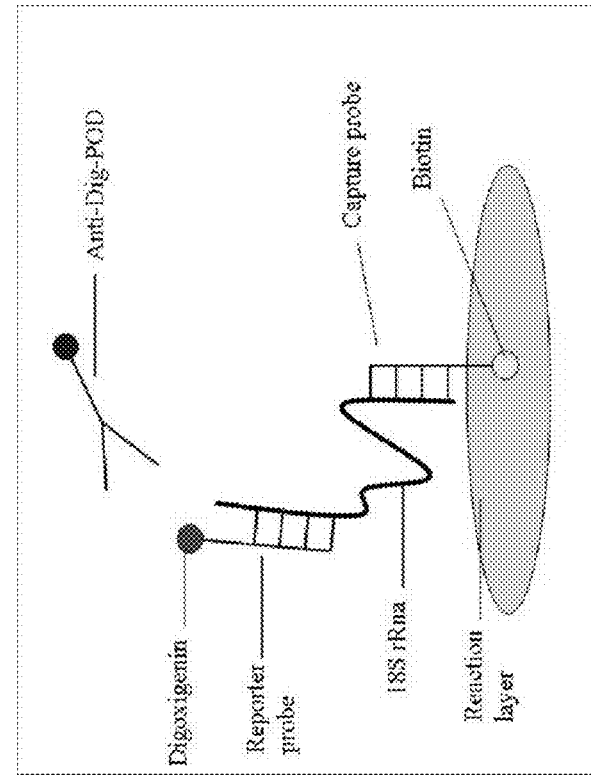
Figure 17B: Detection method for ASO

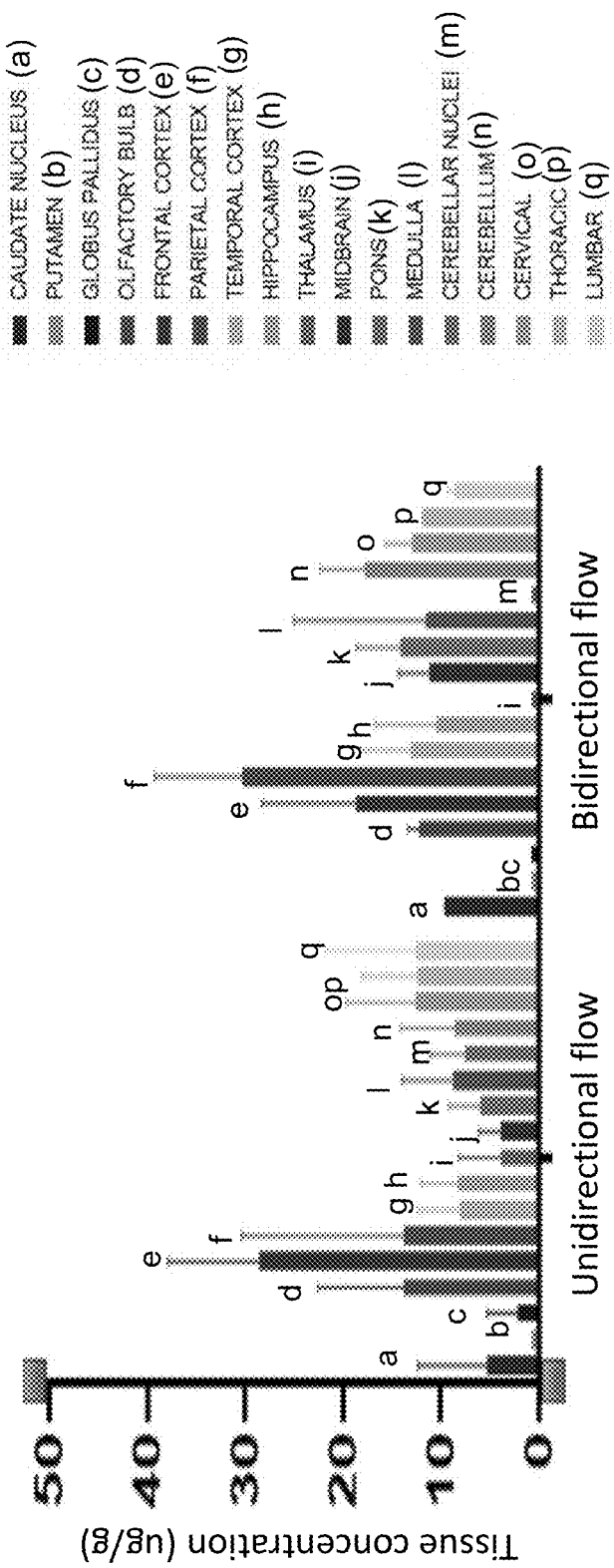
Figure 17C. Tissue levels after Unidirectional or Bidirectional recirculation of ASO

SUBARACHNOID FLUID MANAGEMENT METHOD AND SYSTEM

PRIORITY

This patent application claims priority from provisional U.S. patent application No. 63/084,996, filed Sep. 29, 2020, entitled, "SUBARACHNOID FLUID MANAGEMENT SYSTEM," and naming Gianna Riccardi, William Siopes, Jr., Marcie Glicksman, Anthony DePasqua, Kevin Kalish, and Joshua Vose as inventors, the disclosure of which is incorporated herein, in its entirety, by reference.

This patent application also claims priority from provisional U.S. patent application No. 63/117,975, filed Nov. 24, 2020, entitled, "SUBARACHNOID FLUID MANAGEMENT SYSTEM," and naming Gianna Riccardi, William Siopes, Jr., Marcie Glicksman, Anthony DePasqua, Kevin Kalish, and Joshua Vose as inventors, the disclosure of which is incorporated herein, in its entirety, by reference.

GOVERNMENT RIGHTS

None

FIELD

Illustrative embodiments generally relate to medical devices and methods and, more particularly, illustrative embodiments relate to devices and methods for managing subarachnoid fluid, such as cerebrospinal fluid ("CSF"), and/or drug delivery that may be used to treat neurodegenerative disorders.

BACKGROUND

When delivering a drug intrathecally, it is difficult to ensure that the delivered dosage reaches the target anatomy (e.g., part of the brain correlating to a specific disease, such as the cortical versus subcortical). It also is difficult to verify the actual dosage delivered to the target anatomy, as well as control, in real time, the concentration of the drug in the fluid surrounding the target anatomy.

SUMMARY OF VARIOUS EMBODIMENTS

In accordance with one embodiment of the invention, a CSF management method for use with a patient forms a closed loop CSF circuit between two points on the patient's body. The CSF circuit has a therapeutic inlet to receive a therapeutic material (e.g. a drug), and a pump having a pump outlet to direct CSF along the CSF circuit. The method controls the pump to direct CSF from the pump outlet at a CSF rate that is different from the natural flow rate (i.e., the natural CSF flow rate). The therapeutic material is added to the CSF via the therapeutic input at a therapeutic rate. The CSF rate is different than the therapeutic rate and/or may be greater than the therapeutic rate.

The CSF rate may be a constant rate, or a rate that varies over time. The CSF circuit may be configured so that the CSF simultaneously flows at different rates at two different locations of the CSF circuit. Moreover, the CSF circuit preferably accesses one or more CSF-containing compartments within patient anatomy, such as one or more of the lateral ventricles, the lumbar thecal sac, the third ventricle, the fourth ventricle, and the cisterna magna.

The CSF circuit may have a port into the patient (e.g., a Luer activated valve or other valve). In that case, some embodiments of the CSF circuit have a fluid channel (e.g., a catheter) removably coupled with the port and the pump. To improve performance, the fluid channel also may have a flow sensor, a pressure sensor, or both a flow sensor and a pressure sensor. In addition or alternatively, the fluid channel may have a controller (e.g., an EEPROM) in communication with the pump configured to track the total number of uses of the fluid channel.

In accordance with another embodiment, a CSF management method for use with a patient forms a CSF circuit to control flow of CSF in the body, adds a therapeutic material to the patient's CSF via the CSF circuit, and directs the therapeutic material (e.g., a drug), via the CSF, toward a prescribed portion of the body. Favorably, the method varies the flow of the CSF in the CSF circuit to localize the CSF at the prescribed portion of the body.

To localize, some embodiments may oscillate the flow of CSF within the CSF circuit for a prescribed time and at a prescribed frequency. To that end, the CSF circuit may have a therapeutic delivery pump and a flow control pump. The therapeutic delivery pump may be directly in line with a reservoir of therapeutic material. Some embodiments may vary the CSF flow rate within the CSF circuit at two or more flow rates at two or more different times. As another option, the CSF circuit may produce pulsatile CSF flow.

The CSF circuit preferably is a closed loop channel in communication with the lower abdomen of a human being. As with other embodiments, the CSF circuit may access one or more CSF-containing compartments with patient anatomy, including one or more of the lateral ventricles, the lumbar thecal sac, the third ventricle, the fourth ventricle, and the cisterna magna.

Some embodiments mix, in a mixing chamber, the therapeutic material and the CSF and/or display a control panel interface configured to control one or both of CSF flow rate and an oscillation frequency. The method may track the progression of the therapeutic material as it flows through the CSF circuit. In that case, the method may vary by reducing the CSF flow rate after the therapeutic material contacts the prescribed portion of the body. When imaging the location of the CSF and/or the therapeutic material, the method may localize as a function of the location of the CSF and/or therapeutic material.

As with other embodiments, this embodiment of the CSF circuit may have a port into the patient (e.g., a Luer activated valve or other valve). In that case, some embodiments of the CSF circuit have a fluid channel (e.g., a catheter or a needle) removably coupled with the port and the pump. To improve performance, the fluid channel also may have a flow sensor, a pressure sensor, or both a flow sensor and a pressure sensor. In addition or alternatively, the fluid channel may have a controller (e.g., using an EEPROM) in communication with the pump configured to track the total number of uses, shelf life, or sterilization date of the fluid channel.

Illustrative embodiments add a bolus of therapeutic material, such as a full dose in less than 60 seconds.

In accordance with other embodiments, a CSF fluid conduit (e.g., a catheter) directs CSF flow to or from a patient having an exterior port in fluid communication with that patient's subarachnoid space. The CSF fluid conduit is compatible with a CSF circuit having a pump for controlling CSF fluid flow. Accordingly, to those ends, the CSF fluid conduit has a body forming a fluid traversing bore. The body, which has first and second ends in fluid communication with the bore, are removably couplable between the exterior port of the patient and the pump. The bore is in fluid communication with both the exterior port and pump when removably coupled therebetween. Additionally, the body is configured to form a closed loop CSF channel when removably coupled between the pump and the interface, and the CSF channel and bore are in fluid communication with the patient's subarachnoid space when the body is removably coupled. The CSF fluid conduit also has a flow sensor configured to detect flow through the bore of the body, a pressure sensor configured to detect pressure within the bore of the body, and a controller having a communication channel with the pump. The controller has a usage meter configured to track use of the CSF fluid conduit.

The first end of the body preferably is configured to removably couple with the exterior port of the patient via a removable coupling, such as a conventional ANSI standard Luer lock or needle. In a corresponding manner, the second end of the body may be configured to removably couple with the pump.

The removable coupling can be direct or indirect. For example, it may be an indirect connection and, as such, the fluid circuit may have at least one additional component between the first end and the exterior port of the patient. The at least one additional component thus is between the second port and the pump. Of course, related embodiments may removably couple by directly removably coupling with the specific component.

To manage use of the conduit, the controller may be configured to produce indicia indicating at least one use of the CSF fluid conduit. Moreover, when the bore is configured to receive a therapeutic material mixed with CSF, the controller may be configured to control fluid flow as a function of the therapeutic material. The flow sensor may be configured to detect a variety of items, such as the rate of fluid flow through the bore and/or the total volume of fluid through the bore. Further, the controller may be configured to permit a maximum time to use the CSF fluid conduit. The conduit also may have a programmable logic element configured to be programmed to sense or control use of the CSF fluid conduit.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 1A schematically shows a cerebrospinal fluid circuit that may be used with illustrative embodiments of the invention.

FIG. 1C shows a high level surgical flow process in accordance with illustrative embodiments of the invention.

FIG. 2 schematically shows a two pump circuit with drug fed into pump through separate fluid line in accordance with illustrative embodiments.

FIG. 3 schematically shows a two pump circuit with drug introduced directly into fluid line FIG. 4A schematically shows a flow control valve circuit that may be used with illustrative embodiments.

FIG. 4B schematically shows a syringe pump dosing circuit with a drug introduced directly into the fluid line configured and usable with illustrative embodiments.

FIG. 5 schematically shows a two-pump circuit with a mixing chamber in accordance with illustrative embodiments.

FIG. 6 schematically shows a flow control valve with a mixing chamber in accordance with other embodiments.

FIGS. 7 and 8 schematically show two different user interfaces in accordance with illustrative embodiments.

FIG. 9 shows a process of localizing drug delivery to a target area of the brain in accordance with illustrative embodiments.

FIG. 10 schematically shows directing flow from lumbar to ventricle in accordance with illustrative embodiments.

FIG. 11 schematically shows directing flow from ventricle to lumbar in accordance with illustrative embodiments.

FIG. 12 schematically shows directing flow from lumbar to ventricle with a pulsatile pattern in accordance with illustrative embodiments.

FIGS. 13A and 13B schematically show bidirectional pump circuits that enable flow in two opposite directions (FIG. 13B between right and left ventricles in the brain) in accordance with illustrative embodiments.

FIG. 14 schematically shows another system interface in accordance with illustrative embodiments.

FIG. 15 shows a process of manually programming drug delivery in accordance with illustrative embodiments.

FIGS. 17A, 17B, and 17C detail another example of illustrative embodiments of the invention.

DESCRIPTION OF ILLUSTRATIVE EMBODIMENTS

Figure 1B:
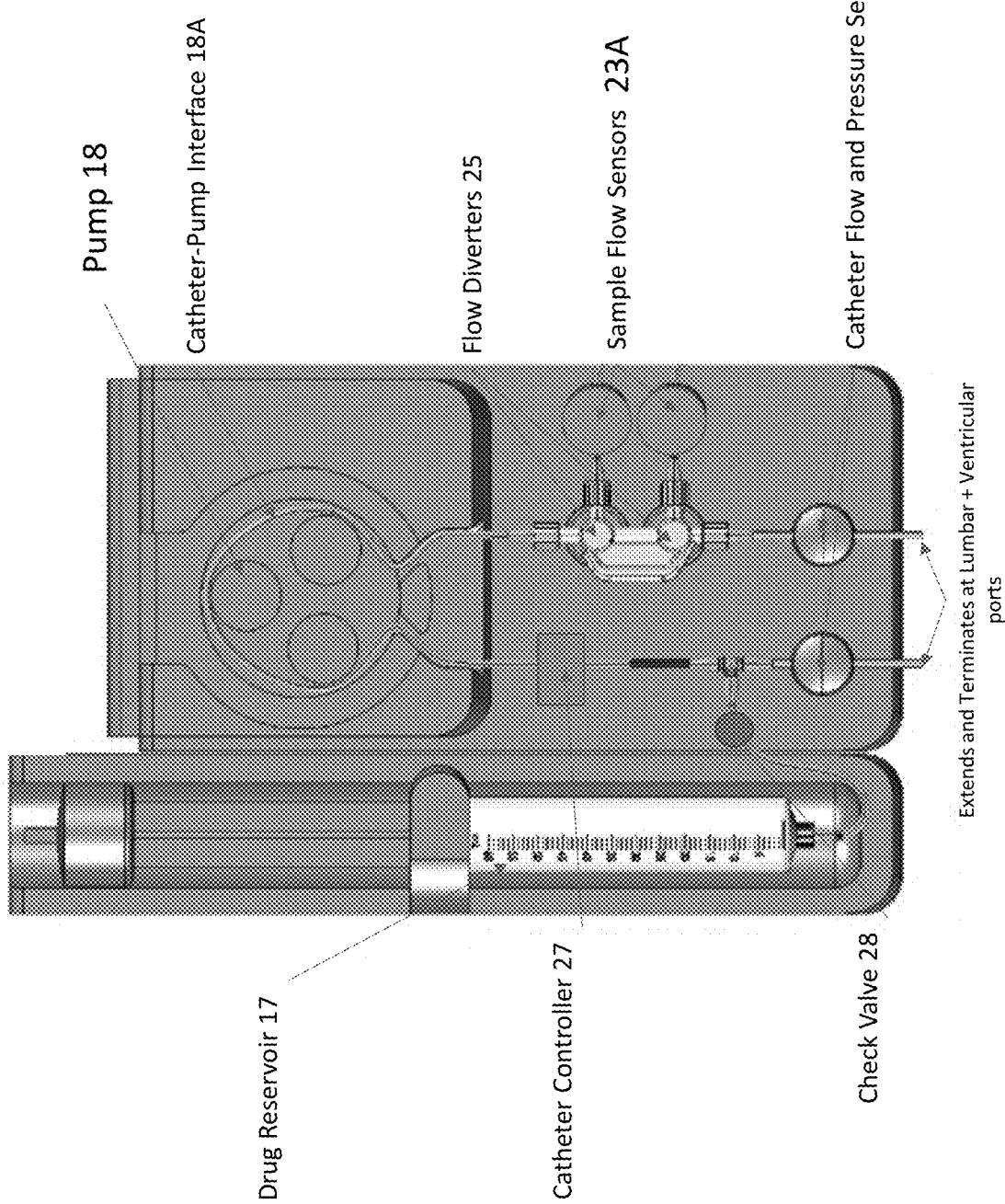
FIG. 1B schematically shows an external catheter configured in accordance with illustrative embodiments.

In illustrative embodiments, a system controllably applies a therapeutic material, such as a drug (e.g., methotrexate, a chemotherapy and immunosuppressive drug) to a specific anatomical location within the subarachnoid space or other area. The therapeutic material, which also may be referred to herein as a "drug," may be applied in a single large volume as a bolus, or dosed gradually over a longer time. To that end, the system has a controller or control system that manages distribution of the therapeutic material within a CSF circuit through which cerebrospinal fluid ("CSF") flows. Specifically, among other things, the controller (or "control system") manages pumps, valves, catheters, and/or other structure(s) to control fluid flow, flow direction, and frequencies of certain periodic flows of bodily fluids (e.g., CSF), to provide a more localized and efficient therapeutic application to a patient.

Preferred embodiments enable the therapeutic material to penetrate the blood-brain barrier by either selecting appropriate CSF and therapeutic material flow rates, and/or controlling CSF flow to maintain a bolus of the therapeutic material within CSF at/near a desired location in the CSF circuit. Consequently, using various embodiments, medical practitioners can be more comfortable applying the appropriate application of the therapeutic in the patient, while reducing toxicity and, in some cases, reducing the need for larger volumes of the therapeutic. Details of illustrative embodiments are discussed below.

Many neurodegenerative diseases have been tied to the accumulation of biomolecules (e.g., toxic proteins) contained in cerebrospinal fluid (CSF) or other fluids (e.g., interstitial fluid) within the subarachnoid space (SAS) of a mammalian subject. Problematically, these (e.g., toxic) biomolecules may be secreted and then transported by the CSF to other cells in the body, which process may occur over the span of years. For example, dipeptide repeat proteins (DPRs) and/or TDP-43 have been implicated in neuronal death in the pathology of amyotrophic lateral sclerosis (ALS, or Lou Gehrig's disease), Alzheimer disease (AD), frontotemporal degeneration (FTD), Parkinson's disease (PD), Huntington's disease (HD), and progressive supranuclear palsy (PSP), to name just a few. Hence, research has focused primarily on the removal of harmful DPRs. Techniques for removing DPRs and/or TDP-43 have included: shunting CSF from the CSF space, diluting the CSF (e.g., with an artificial fluid), administering a drug into the CSF, conditioning the CSF, and/or manipulating CSF flow.

Recent breakthrough techniques for handling this problem include ameliorating the CSF, and treating a neurological disorder by removing or degrading a specific (toxic) protein.

Amelioration, as used in various embodiments, involves systems and methods for ameliorating a fluid in the subarachnoid space (SAS) (e.g., a cerebrospinal fluid (CSF), an interstitial fluid (ISF), blood, and the like) of a mammalian subject, unless otherwise particularly distinguished (e.g., referred to as solely CSF). Representative systems may be completely or partially implanted within the body of the mammalian subject (discussed below). Within the body, the systems and/or components thereof may also be completely or partially implanted within the SAS and exposed to the exterior via a port 16 (e.g., a medical valve that provides selective access to the interior system components). These systems execute processes that may occur entirely in-vivo, or some steps that occur extracorporeally. Illustrative embodiments ameliorate with a CSF circuit, discussed below.

Amelioration, for the purpose of illustration, may include changing the physical parameters of the fluid, as well as digestion, removal, immobilization, reduction, and/or alteration, to become more acceptable and/or inactivation of certain entities, including: target molecules, proteins, agglomerations, viruses, bacteria, cells, couples, enzymes, antibodies, substances, and/or any combination thereof. For example, in some embodiments and applications, amelioration may refer to removing toxic proteins from or conditioning one or more of the blood, interstitial fluid, or glymph contained therein, or other fluid, as well as the impact that this removal has on treating diseases or conditions that affect various bodily functions, (i.e., improving the clinical condition of the patient). Moreover, amelioration may be performed by any one of: digestion, enzymatic digestion, filtration, size filtration, tangential flow filtering, countercurrent cascade ultrafiltration, centrifugation, separation, magnetic separation (including with nanoparticles and the like), electrophysical separation (performed by means of one or more of enzymes, antibodies, nanobodies, molecular imprinted polymers, ligand-receptor complexes, and other charge and/or bioaffinity interactions), photonic methods (including fluorescence-activated cell sorting (FACS), ultraviolet (UV) sterilization, and/or optical tweezers), photoacoustical interactions, chemical treatments, thermal methods, and combinations thereof. Advantageously, various embodiments or implementations of the present invention may reduce levels of toxicity and, after reduced, facilitate maintaining the reduced levels over time.

The extent of amelioration, as reflected by the concentration of the target biomolecules, may be detected through a variety of means. These include optical techniques (e.g., Raman, coherent Stokes, and anti-Stokes Raman spectroscopy; surface enhanced Raman spectroscopy; diamond nitrogen vacancy magnetometry; fluorescence correlation spectroscopy; dynamic light scattering; and the like) and use of nanostructures such as carbon nanotubes, enzyme linked immunosorbent assays, surface plasmon resonance, liquid chromatography, mass spectrometry, circular proximity ligation assays, and the like.

Amelioration may include the use of a treatment system (e.g., UV radiation, IR radiation), as well as a substance, whose properties make it suitable for amelioration. Amelioration of CSF or ameliorated CSF—which terms may be used interchangeably herein—refers to a treated volume of CSF in which one or more target compounds have been partially, mostly, or entirely removed. It will be appreciated that the term removed, as used herein, can refer not only to spatially separating, as in taking away, but also effectively removing by sequestering, immobilizing, or transforming the molecule (e.g., by shape change, denaturing, digestion, isomerization, or post-translational modification) to make it less toxic, non-toxic or irrelevant.

The term, "ameliorating agent" generally refers to a material or process capable of ameliorating a fluid, including enzymes, antibodies, or antibody fragments, nucleic acids, receptors, anti-bacterial, anti-viral, anti-DNA/RNA, protein/amino acid, carbohydrate, enzymes, isomerases, compounds with high-low biospecific binding affinity, aptamers, exosomes, ultraviolet light, temperature change, electric field, molecular imprinted polymers, living cells, and the like. Additional details of amelioration are taught by PCT Application No. PCT/US20/27683, filed on Apr. 10, 2020, the disclosure of which is incorporated herein, in its entirety, by reference. In a similar manner, details for further treatments are taught by PCT Application No. PCT/US19/042880, filed Jul. 22, 2019, the disclosure of which is incorporated herein, in its entirety, by reference.

To control CSF flow within the body (e.g., through the ventricle), illustrative embodiments form a CSF circuit/channel (identified by reference number "10") that manages fluid flow in a closed loop. FIG. 1A, for example, shows one embodiment of such a CSF circuit 10. In this example, internal catheters 12 positioned in-vivo/interior to the body fluidly couple together via the subarachnoid space. To that end, a first internal catheter 12 fluidly couples a prescribed region of the brain (e.g., the ventricle) to a first port 16, which itself is configured and positioned to be accessible by external components. In a corresponding manner, a second catheter couples the lumbar region or the lower abdomen of the subarachnoid space with a second port 16 that, like the first port 16, also is configured to be positioned and accessible by external components. The first and second ports 16 may be those conventionally used for such purposes, such as a valved Luer-lock or removable needle. The first and second internal catheters 12 thus may be considered to form a fluid channel extending from the first port 16, to the ventricle, down the spine/subarachnoid space to the lumbar, and then to the second port 16. These internal components, which may be referred to as "internal CSF circuit components," are typically surgically implanted by skilled professionals in a hospital setting.

The CSF circuit 10 also has external components (referred to as "external CSF circuit components). To that end, the external CSF circuit components include at least two fluid conduits 14. Specifically, the external CSF circuit components include a first external fluid conduit 14, that couples with the first port 16 for access to the ventricle. The other end of the first external conduit 14 is coupled with a management system 19, which includes one or more CSF pumps (all pumps are generically identified in the figures as reference number "18"), one or more user interface/displays 20, one or more drug pumps 18, and a control system/controller 22. The fluid external fluid conduit 14 may be implemented as a catheter and thus, that term may be used interchangeably with the term "conduit" and be identified by the same reference number 14.

Illustratively, this management system 19 is supported by a conventional support structure (e.g., a hospital pole 24 in FIG. 1A). To close the CSF circuit 10, a second external catheter 14 extends from that same CSF management system 19 and couples with the second port 16 and the management system 19. This management system 19 and external catheters 14 therefore form the exterior part of a closed CSF circuit 10 for circulating the CSF and therapeutic material.

It should be noted that the CSF circuit 10 may have one or more components between the first and second ports 16 and the respective removable connections of the first and second external catheters 14. For example, the first port 16 may have an adapter that couples with the first external catheter 14, or another catheter with a flow sensor may couple between such external catheter 14 and port 16. As such, this still may be considered a removable connection, albeit an indirect fluid connection. There may be corresponding arrangements with the other end of the first external catheter 14, as well as corresponding ends of the second external catheter 14. Accordingly, the connection can be a direct connection or an indirect connection.

The first and second external catheters 12 and 14 preferably are configured to have removable connections/couplings with the management system 19, as well as their respective ports 16. Examples of removable couplings may include a screw-on fit, an interference fit, a snap-fit, or other known removable couplings known in the art. Accordingly, a removable coupling or removable connection does not necessarily require that one forcibly break, cut, or otherwise permanently break the ports 16 for such a connection or disconnection. Some embodiments, however, may enable a disconnection from the first and/or second ports 16 via breaking or otherwise, but the first and/or second ports 16 should remain in-tact to receive another external catheter 14 (e.g., at the end of life of the removed external catheter 14).

FIG. 1B schematically shows more details of the first and/or second external conduits/catheters 14. This figure shows an example of an external catheter 14 operating with other parts of the system. As shown, the system receives a drug reservoir 17 (e.g., a single-use syringe) configured to deliver a dose of therapeutic material (e.g., a drug) that fluidly couples with the catheter 14 via a check valve 28 and T-port on the catheter 14. In addition, the catheter 14 is coupled with a mechanical pump 18 and also preferably includes a sample port 23 with flow diverters 25 for diverting flow toward or away from a sample port 23. The sample port 23 preferably has sample port flow sensors 23A to track samples.

Some embodiments may be implemented as a simple catheter having a body forming a fluid-flow bore with removably couplable ends (or only one removably couplable end). Illustrative embodiments, however, add intelligence to make one or both of these external catheters 14 "smart" catheters, effectively creating a more intelligent flow system. For example, either one or both of the external catheters 14 can have a processor, ASIC, memory, EEPROM (discussed below), FPGAs, RFID, NFC, or other logic (generally identified as reference number "27") configured to collect, manage, control the device, and store information for the purposes of security, patient monitoring, catheter usage, or communicating with the management system 19 to actively control fluid dynamics of the CSF circuit 10. Among other things, the management system 19 may be configured to coordinate with an EEPROM 27 to control CSF fluid flow as a function of the therapeutic material infusion flow added to the CSF circuit 10 (discussed below) via the check valve 28 at the output of the drug reservoir 17.

As shown in FIG. 1B, one embodiment of the external catheter 14 has the noted electrically erasable programmable read-only memory, EEPROM 27, (or other logic/electronics) that can be implemented to accomplish a variety of functions. Among others, the EEPROM 27 can ensure that the CSF circuit 10 and its operation is customized/individualized to a patient, a treatment type, a specific disease, and/or a therapeutic material. For example, in response to reading information stored in the EEPROM 27, the control system 22 may be configured to control fluid flow as a function of the therapeutic material.

Importantly, as a disposable device, the EEPROM 27 or other logic of the external catheter 14 can be configured to provide alerts, and/or produce or cause production of some indicia (e.g., a message, visual indication, audio indication, etc.) indicating that the external catheter 14 has reached an end of its lifecycle, or indicating how much of its lifecycle remains. For example, an external surface of the catheter 14 may have a tag that turns red when the EEPROM 27 and/or other logic 27 determines that the external catheter 14 has reached its full lifetime use. For example, the external catheter 14 may be considered to have a usage meter, implemented as some logic or EEPROM 27, configured to track use of the CSF fluid conduit 14 to help ensure it is not used beyond its rated lifetime. Moreover, the logic or EEPROM 27 can register with the control system 22 to start use timers to reduce tampering or use beyond a lifetime.

Some embodiments have a printable circuit board (PCB) equipped with a wireless interface (e.g., Bluetooth antenna) or a hardware connection configured to communicate the pump 18 and/or control system 22. The external catheter 14 can be configured to time out after a certain period, capture data, and communicate back and forth with the control system 22 or other off-catheter or on-catheter apparatus to share system specifications and parameters. The intelligent flow catheter 14 can be designed with proprietary connections such that design of knockoffs or cartridges 26 (discussed below) can be prevented to ensure safety and efficacy of the CSF circuit 10 and accompanying processes.

In addition to the management logic, the external catheter(s) 14 also may have a set of one or more flow sensors and/or a set of one or more pressure sensors. Both of those flow sensors are shown generically at reference number 29, and may be located upstream or downstream from their locations in FIG. 1B. For example, the left sensor(s) 29 generically shown in FIG. 1B can be a flow sensor, pressure, or both a flow sensor and pressure. The same can be said for the right sensor(s) 29 generically shown in FIG. 1B. They preferably are positioned between the ports 16 on the body and the remaining components as shown.

Of course, the flow sensor(s) 29 may be configured to detect flow through the bore of the catheter body, while the pressure sensor(s) 29 may be configured to detect pressure within the bore of the body. Among other functions, the flow sensor(s) 29 may monitor flow rate of fluid through the conduit bore and/or total flow volume through the conduit bore.

The catheter 14 preferably is configured to have different hardness values at different locations. Specifically, illustrative embodiments may use a mechanical pump 18, as shown and noted above. The pump 18 may periodically urge a compressive force along that portion of the catheter 14 it contacts at its interface 18A with the catheter 14. The outlet of the pump 18 in this case may be the portion of the catheter 14 that is receiving the output of a neighboring compressed catheter portion (e.g., a portion that is adjacent to the compressed catheter portion(s). To operate efficiently, illustrative embodiments form the catheter 14 to have a specially configured hardness at that location (e.g., 25-35 Shore A). Diameter also is important for flow and thus, one skilled in the art should determine appropriate diameters as a function of performance and durometer/hardness. Preferably, the catheter portion that contacts the pump 18 is softer than the remainder of the catheter 14, although both could have the same hardness. Accordingly, the catheter preferably has a variable hardness along its length and may even have a variable diameter.

Alternative embodiments may provide an open-loop CSF fluid circuit 10. For example, the CSF fluid circuit 10 may have an open bath (not shown) to which fluid is added and then removed. The inventors expect the closed-loop embodiment to deliver better results, however, than those of the open-loop CSF fluid circuit 10.

Illustrative embodiments are distributed to healthcare facilities and/or hospitals as one or more kits. For example, one more inclusive kit may include the internal and external catheters 12 and 14. Another exemplary kit may include just the internal catheters 12 and the ports 16 (e.g., for a hospital), while a second kit may have the external catheters 14 and/or a single-use syringe. Other exemplary kits may include the external catheters 14 and other components, such as the management system 19 and/or a CSF treatment cartridge 26. See below for various embodiments of the CSF circuit 10 and exterior components that also may be part of this kit.

Accordingly, when coupled, these pumps 18, valves (discussed below and all valves generally identified by reference number 28), internal and external catheters 14, and other components may be considered to form a fluid conduit/channel that directs CSF to the desired locations in the body. It should be noted that although specific locations and CSF containing compartments are discussed, those skilled in the art should recognize that other compartments can be managed (e.g., the lateral ventricles, the lumbar thecal sac, the third ventricle, the fourth ventricle, and/or the cisterna magna). Rather than accessing the ventricle and the lumbar thecal sac, both lateral ventricles could be accessed with the kit. With both internal catheters 12 implanted, CSF may be circulated between the two lateral ventricles, or a drug could be delivered to both ventricles simultaneously.

In illustrative embodiments, the CSF management system 19 generally manages fluid flow to target anatomy through the CSF circuit 10. To that end, that management system 19 has at least one pump 18 that directs flow of the CSF, and at least one pump 18 that directs flow of a therapeutic material (e.g., a drug) though the CSF circuit 10 to desired anatomy. Alternative embodiments may have more pumps 18 for these functions, or combine pumps 18 for these functions. The management system 19 also has a plurality of valves 28 to control flow, and the control system 22, as noted, is configured to control the pumps 18 to selectively apply the drug-carrying CSF to desired local anatomy. FIG. 1A also shows a user interface 20 that enables a clinician to control drug and fluid parameters in the CSF circuit 10 (discussed below) via the control system 22.

Some embodiments may use a monitoring process, such as real-time spectroscopy, to monitor drug concentrations in the CSF. In some of these embodiments, a spectrophotometric sensor may be placed in the CSF circuit 10 to measure the localized concentration of a substance based on its absorption at various wavelengths. For example, some embodiments may use a sensor constructed to measure a single wavelength or multiple wavelengths. The reading taken by the sensor may be relayed to the control system 22, where it would then be stored or processed for various purposes. This signal could be processed for a number of purposes, such as to trigger the control system 22 to alter the fluid flow, flow direction, and/or frequencies of certain periodic flows of bodily fluids (e.g., CSF) to provide a more localized and efficient therapeutic application to a patient in real-time. It will be appreciated that the signal could also be stored or displayed such that the changes to flow, direction or frequencies of period flows could be adjust manually.

FIG. 1C shows a high level surgical flow process that may incorporate the CSF circuit 10 of FIG. 1A in accordance with illustrative embodiments of the invention. It should be noted that this process is substantially simplified from a longer process that normally would be used to complete the surgical flow. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 100 by setting up the internal catheters 12 inside the patient. To that end, step 100 accesses the ventricles and thecal sacs using standard catheters and techniques, thus providing access to the CSF. Step 102 then connects access catheters 12 to peritoneal catheters 12, which are tunneled subcutaneously to the lower abdomen. The tunneled catheters 12 then are connected at step 104 to the ports 16 implanted in the abdomen.

At this point, the process sets up an extracorporeal circulation set (i.e., the external catheters 14, or the "smart catheters" in some embodiments). To that end, step 106 may prime and connect the extracorporeal circulation set 14 to the subcutaneous access ports 16. Preferably, this step uses an extracorporeal circulation set, such as one provided by Endear Therapies, Inc. of Newburyport, MA, and/or the external catheters 14 discussed above. The process continues to step 110, which connects an infusion line or other external catheter 14 to the management system 19, and then sets the target flow rate and time. At this point, setup is complete and treatment may begin (step 112).

The process then removes endogenous CSF from the ventricle. This CSF may then be passed through a digestion region (e.g., through a cartridge 26 having a specific digesting material), where certain target proteins in the CSF are digested. For example, the cartridge 26 may have an inner plenum space 1830 of the cartridge 26 filled with a plurality of (e.g., porous, chromatography resin) beads that have been compression packed. To prevent constituents from entering or escaping from the cartridge 26, a filter membrane may be disposed at the first end of the cartridge 26 and a second filter membrane may be disposed at the second end of the cartridge 26. In some applications, the ameliorating agent may be decorated on the beads 1835.

In some applications, the cartridge 26 may be compression packed with a chromatography resin (e.g., agarose, epoxy methacrylate, amino resin, and the like) that has a protease covalently bonded (i.e. immobilized) to the three-dimensional resin matrix. The selected protease may be configured to degrade and/or removing target toxic biomolecules by way of proteolytic degradation. The resin may be a porous structure having a particle size commonly ranging between 75-300 micrometers and, depending on the specific grade, a pore size commonly ranging between 300-1800 Å. Thus, at a high level, the cartridge 26 has ameliorating agent that removes and/or substantially mitigates the presence of toxic proteins from the CSF.

This and similar embodiments may consider this to be an input for the digesting enzyme. Any location providing access to the drug may be considered to be an input for the drug. At step 116, the treated CSF exits the digestion region and is returned via the CSF circuit 10 to the lumbar thecal sac. The process concludes at step 118, which stops the pump 18 when treatment is complete. The management system 19 then may be disconnected and the ports 16 flushed.

In accordance with illustrative embodiments, the CSF circuit 10 is configured to improve the likelihood of the drug passing through the blood-brain barrier. To that end, the management system 19 enables the user or logic to independently set both the flow rate of CSF circulation (e.g., between 0.05 ml/min and 2.0 ml/min, such as 0.5 ml/min) and the dosing rate of the drug (e.g., between 0.01 ml/min to 2.0 ml/min, such as 0.02 ml/min). Preferably, these rates are different, although they can be the same. In illustrative embodiments, the CSF circulation rate is controlled to be different from the natural CSF flow rate. Note that the natural CSF flow rate is the rate of CSF flow without intervention by outside equipment, such as the pumps 18 and other CSF circuit components—even if it is within a range of typical non-interventionally controlled CSF flow rates. Thus, unless the context dictates otherwise, the non-natural CSF flow rate is the flow rate with such intervention. In other embodiments, the CSF flow rate is simply changed from its truly natural flow rate—i.e., the rate at which the CSF flows without intervention.

Depending on a number of factors, the CSF flow rate may be greater than the rate of drug infusion, while in other embodiments, the CSF flow rate is less than rate of the drug infusion rate. Other embodiments may set them to be equal. Those skilled in the art can select the appropriate flow rate based on a variety of factors, including the drug being delivered, the illness, patient profile, rated pressure of the CSF circuit 10, etc.

The inventors recognized that varying the two rates in a coordinated manner enables more control of the drug dose as well as more control of the drug treatment time. Stated another way, these two independent flow rates enable setting of the dosing rate, which allows the user to optimize drug concentration. At the same time, having the ability to set the flow rate allows the user to control the rate of delivery (as opposed to relying upon natural CSF flow).

As noted in the example below, the inventors were surprised to discover that varying the rates in this manner enabled penetration of the drug across the otherwise difficult to penetrate blood-brain barrier. The selected CSF flow rate may be constant or variable. For example, the CSF flow rate may be set to a first rate for a first period of time, a second rate for a second period of time, and a third rate for a third period of time. As such, various embodiments enable flow of the CSF within the CSF circuit 10 at two or more flow rates at two or more different times. The drug delivery rate may be constant or variable in a similar manner, but coordinated with the CSF flow rate to deliver preferred results.

The inventors recognized that a wide variety of different CSF circuit configurations can accomplish the desired goals. FIG. 2 schematically shows a two pump CSF circuit 10 with the drug fed into the pump 18 through a separate fluid line/catheter 12/14 in accordance with illustrative embodiments. In a corresponding manner, FIG. 3 schematically shows a two pump CSF circuit 10 with drug introduced directly into fluid line.

In one embodiment, the CSF circuit 10 has two pumps 18, Pump 1 and Pump 2, to enable a user to set flow rate and dosing rate independently. To that end, Pump 1 may be programmed to control the rate of CSF circulation, while Pump 2 may be programmed to control the dosing rate of the drug to be delivered. Both pumps 18 could be programmed to achieve a desired delivery profile. Check valves 28 or other flow control devices prevent backflow into either pump 18.

As show, the drug may be fed into the pump 18 through a separate fluid line/catheter (FIG. 2) and input to mix with the patient's CSF in the internal catheter/tubing set 12 before being reintroduced to the body. Alternatively, the drug may also be pre-loaded into a cartridge 26 or other type of drug reservoir and connected directly into the fluid line/catheter 14 (FIG. 3). In this latter embodiment, the CSF mixes with the drug as it flows through the cartridge 26 and tubing set 12/14. FIG. 4A schematically shows another embodiment in which a flow control valve 28 is used in place of Pump 2. In this embodiment, that flow control valve 28 preferably is programmed to control the dosing rate (i.e., the rate of adding the drug to the CSF circuit 10 carrying the CSF.

FIG. 5 schematically shows a two-pump circuit 10 with a mixing chamber 30 in accordance with illustrative embodiments. In particular, to ensure a homogeneous mixture of CSF and the drug being delivered, the noted mixing chamber 30 is added to both the two-pump circuit 10 (FIG. 5) and the flow control valve 28 circuit (FIG. 6). The mixing chamber 30 can contain a sensor that provides a readout of a drug's concentration in the CSF, or the management system 19 could simply be programmed to produce a specific drug concentration in the CSF.

In FIG. 5, the CSF-circulating pump 18 and the dosing pump 18 (via an input) feed into the mixing chamber 30 at independent programmable rates. Upon entering the chamber, a small turbine mixes the fluids and the homogeneous mixture is expelled and returned to the patient anatomy. The same concept applies to FIG. 6, but some in-line mixing occurs before the fluids reach the mixing chamber 30.

Whether controlling dosing rate by a second pump 18 or by a flow control valve 28, CSF delivery may be manually programmed on an interface/display 20 similar to FIGS. 7 and 8. Specifically, FIGS. 7 and 8 schematically show two different user interfaces 20 in accordance with illustrative embodiments. Rather than requiring the user to input a dosing rate, however, the user may specify a drug concentration and the management system 19 responsively may adjust the dosing rate accordingly to achieve that concentration. The user can also input a maximum dosage. After this dosage was reached, the management system 19 would automatically stop treatment. FIG. 8 shows one such interface 20 (e.g., a graphical user interface or a manual interface).

It should be noted that the during actual processing, the CSF flow rate may differ at different parts of the CSF circuit 10—total CSF flow rate in the CSF circuit 10 is not necessarily homogenous. For example, some parts of the CSF circuit 10 may be wider (e.g., certain human geographies) and thus, may be slower than the average CSF circuit flow rate, while other portions may be narrower, causing a nozzle effect and increasing the CSF flow rate at that point. Near the pump 18 (e.g., at the pump output), however, the CSF flow rate can be controlled to provide a desired rate across the entire CSF circuit 10, even if that rate may deviate in local parts of the CSF circuit.

The discussion above relates to delivering a therapeutic material, such as a drug, over a longer infusion period (e.g., 5 minutes, 10 minutes, 30 minutes, 1-6 hours, days, etc.). FIG. 9 shows another embodiment that localizes drug delivery at a target area of the brain using a bolus drug infusion. Specifically as known by those in the art, a dose of drug can be delivered in a short time period (e.g., 10 seconds, 20 seconds, 60 seconds), or over a longer period (i.e., gradual drug administration, as noted above). The shorter drug delivery is known in the art as a "bolus" drug delivery.

Specifically, to optimize delivery, FIG. 9 alternates the flow direction of the pump 18. The pump 18 thus has programmable controls, via the control system 22, for flow rate and frequency of these alternations. The flow rate and frequency preferably are programmed to achieve a desired delivery profile.

In a manner similar to the other process discussed above, the process of FIG. 9 is substantially simplified from a longer process that normally would be used to complete the localize drug delivery. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

FIG. 9 therefore delivers a drug intrathecally using positive displacement at a desired flow rate. It may incorporate the components discussed above, as well as principles discussed for other embodiments, such as that discussed above with regard to FIG. 2. The process of FIG. 9 begins at step 900 by adding the drug in a bolus dose to the CSF circuit 10, and/or administering a tag for imaging to the drug. In the latter example, its position can then be tracked using standard imaging techniques to determine when the drug has reached the target anatomy. Alternative embodiments add the drug to the CSF without administering a tag. Such steps may use other techniques to ensure the drug is localized at the desired target anatomy.

Step 902 sets the desired flow rate, direction, timing, and other parameters for the CSF circuit 10 to accomplish the bolus application. For example, specific computer program code on a tangible medium within the control system 22 may cooperate with other components of the CSF circuit 10 to control addition of the therapeutic material, localize the therapeutic material, or both. Next, after step 904 verifies the position of the drug at a target anatomy, step 906 controls the pump 18 to maintain the drug at that target location. Among other ways, step 906 may control the pump(s) 18 to oscillate at a desired flow rate and frequency to contain the drug at that prescribed or desired anatomical location for a pre-set period of time.

After the bolus reaches the target anatomy, the pump 18, which can be programmable and/or have logic, can reverse CSF flow; specifically, the pump 18 can alternate quickly between pushing and pulling flow of the CSF so that the bolus of drug is localized to the target anatomy in the brain (or another target anatomy). In other words, the higher concentration of drug in a portion of the CSF can moved back and forth over the target region. Other embodiments can simply slow down the CSF flow rate to ensure a longer drug application to the target. Either way, these embodiments preferably "soak" the target with the drug, providing a higher quality drug administration. As a result, despite using less of the drug than would be administered by prior art systems, this embodiment still administers a desired amount of the drug to the target by this localizing technique, consequently minimizing toxicity and drug costs (step 908).

It should be noted that "reaching" the target anatomy may be defined by the user or other entity within the control system 22. For example, the portion of CSF in the CSF circuit 10 having the higher concentration of drug (from the bolus) may be considered to have reached the target anatomy when some identifiable portion of it (e.g., the highest concentration, or an interior point within the spread of the drug in the CSF) may be within a prescribed distance upstream of the target, or a prescribed distance downstream of the target. Some embodiments may require the defined portion of CSF with the high drug concentration to actually be at or in contact with that target region. Other embodiments may consider the drug to have "reached" the target simply by calculating the time it should take to reach that area, using artificial intelligence/machine learning, and/or through empirical studies.

Illustrative embodiments can be implemented in a number of different manners with catheters 12/14, pumps 18, valves 28, etc. similar to those discussed above (including the noted external catheters 14). FIGS. 10-14 show several exemplary implementations. In the embodiment shown in FIG. 10, the CSF circuit 10 has four pinch valves 28 on tubing (i.e., external catheters 14), enabling fluid oscillation between opposing flow directions. To flow from lumbar to ventricle (FIG. 10), pinch valves 1 and 2 are opened while pinch valves 3 and 4 are closed. Conversely, to switch flow direction from ventricle to lumbar (FIG. 11), pinch valves 1 and 2 are closed while pinch valves 3 and 4 are opened. Controlling the pinch valves 28 in this manner enables flow direction oscillation. The frequency at which the pinch valves 28 switched between open and closed may be set by the user as could the flow rate of the pump 18 (e.g., via the control system 22). Alternative embodiments may pre-program such parameters into the management system 19.

In fact, the same pinch valve 28 configuration (FIG. 12) may be used to create a pulsatile flow pattern. For example, when flowing from lumbar to ventricle, pinch valves 3 and 4 remain closed, while pinch valves 1 and 2 are pulsed (i.e., periodically switched between open and closed) at a frequency set by the user.

The ability to set the frequency at which the pinch valves 28 open and close enables a range of pulsatile effects to be implemented. For example, rather than rapidly switching between open and closed pinch valves 28, the valves 28 can remain closed long enough to build up a set pressure in the fluid line. Shortly after opening the pinch valves 28, a bolus of the drug can be released as a result of the pressure build-up.

Flow direction oscillation and a pulsatile flow pattern could also be produced using a bidirectional pump 18 instead of using pinch valves 28 (e.g., FIG. 13A and FIG. 13B). The pump 18 can be programmed to switch flow directions at a frequency set by the user. While flowing in one direction, the pump 18 can be programmed to pulse by starting and stopping at a frequency also set by the user. Those skilled in the art may use other techniques to provide bidirectional flow.

In addition to those noted above, some embodiments may set the frequency, flow rate, and other parameters as a function of the requirements and structure of the anatomy and devices used in the treatment (e.g., in the CSF circuit 10). Among others, those requirements may include the diameter of the catheters in the CSF circuit 10, physical properties of the drug, the interaction of the drug at the localized region, the properties of the localized region, and other requirements and parameters relevant to the treatment. Those skilled in the art may select appropriate parameters as a function of the requisite properties.

FIG. 14 schematically shows another system interface 20 configured in accordance with illustrative embodiments. Specifically, whether controlling delivery parameters by pinch valve, a bidirectional pump 18, or other means, the delivery profile can be controlled manually with an interface 20, such as the interface 20 shown in FIG. 14, and/or a delivery profile loaded onto the management system 19. As with the other interfaces, this interface 20 may be a fixed control panel, or a graphical user interface on a display device.

FIG. 15 shows a process of manually programming drug delivery of a bolus in accordance with illustrative embodiments. In a manner similar to the other process discussed above, this process is substantially simplified from a longer process that normally would be used to complete the localize drug delivery. Accordingly, this process may have many additional steps that those skilled in the art likely would use. In addition, some of the steps may be performed in a different order than that shown, or at the same time. Those skilled in the art therefore can modify the process as appropriate. Moreover, as noted above and below, many of the materials, devices, and structures noted are but one of a wide variety of different materials and structures that may be used. Those skilled in the art can select the appropriate materials and structures depending upon the application and other constraints. Accordingly, discussion of specific materials, devices, and structures is not intended to limit all embodiments.

The process begins at step 1500, which sets the flow direction. Three options include lumbar to ventricle (1502A), ventricle to lumbar (step 1502B), or oscillating between flow directions (step 1502C). Next, the process sets the flow rate at steps 1504A or 1504B, and sets the frequency of the pulse (step 1506A) or oscillation frequency (step 1506B). Alternative embodiments can be programmed using artificial intelligence algorithms or other program logic.

Figure 16A:
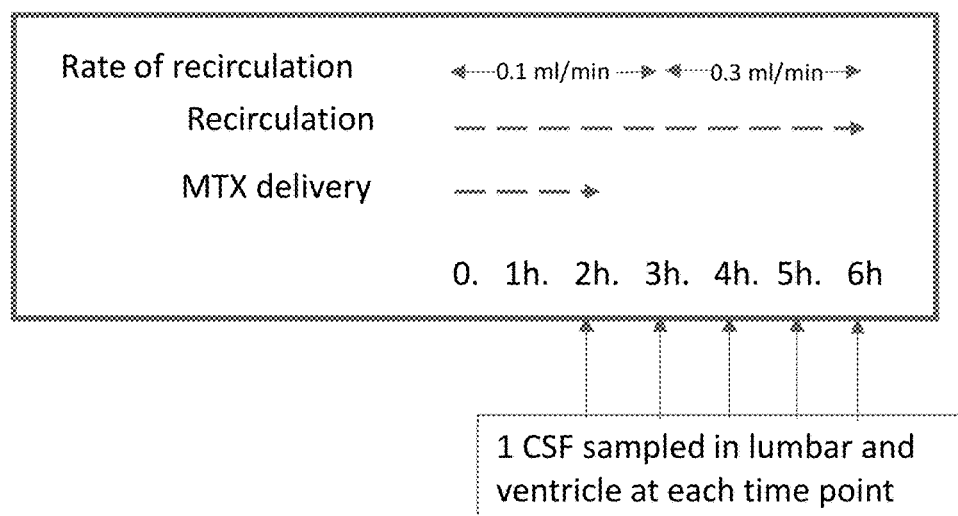
FIGS. 16A, 16B, and 16C detail an example of illustrative embodiments of the invention.
Figure 16B:
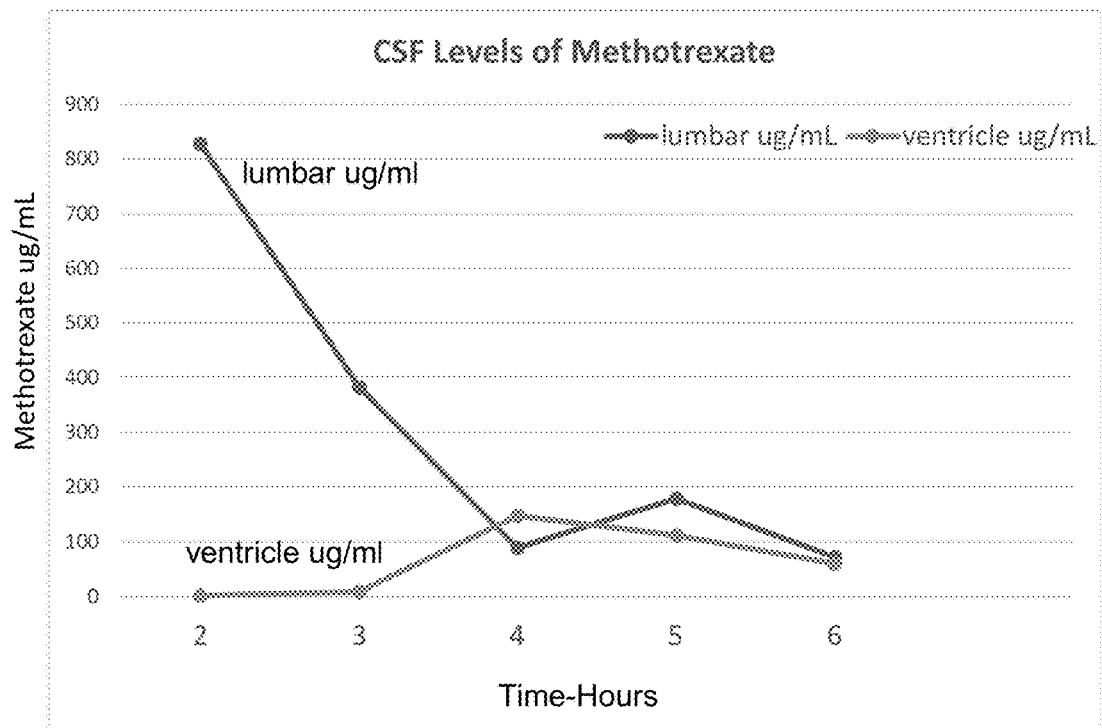
Figure 16C:
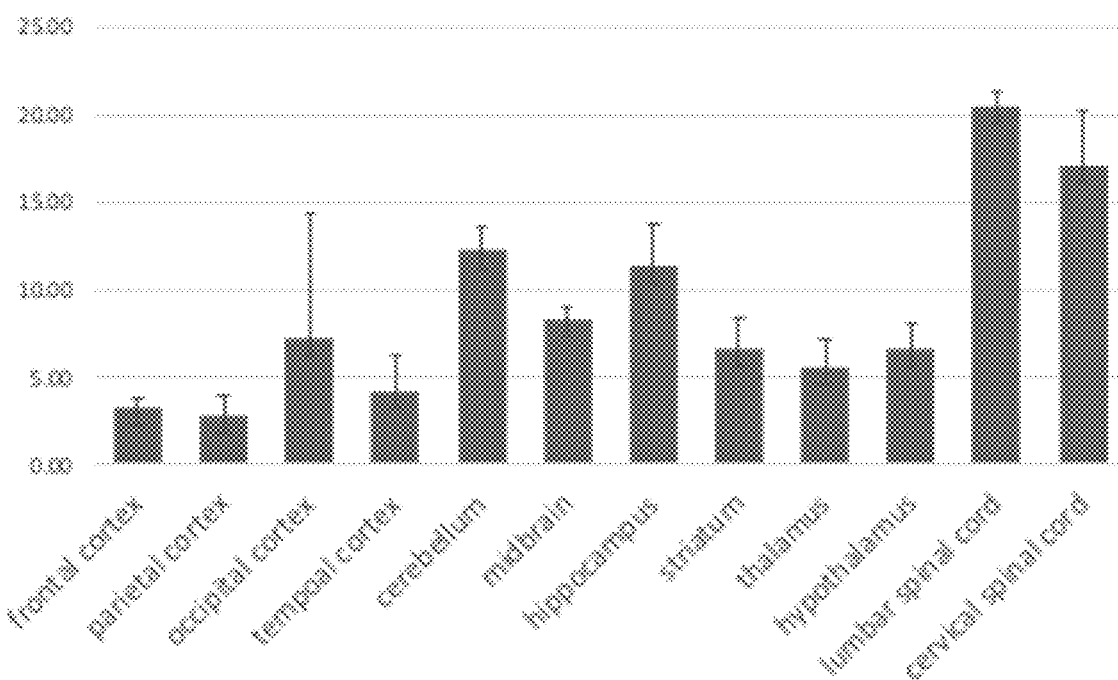

Example 1: Administration of Methotrexate to a Sheep Using Illustrative Embodiments The inventors administered methotrexate to sheep using illustrative embodiments. An outline of the study is depicted by FIGS. 16A-16C. A sheep used for this experiment received the CSF circuit 10 of illustrative embodiments. Circulation was started at the same time that methotrexate was infused. Methotrexate was infused at a gradual rate of 2 mLs over 2 minutes and then recirculation from lumbar to ventricle was started at a rate of 0.2 mLs/min. Circulation continued after drug infusion was stopped for four more hours. At zero to three hours, the circulation rate was at 0.1 mL/min and from four to six hours, circulation was at 0.3 mL/min. The dose of methotrexate infused was 12 mg. Drug concentration was measured with LC/MS (liquid chromatography with the mass analysis capabilities of mass spectrometry) in the CSF, spinal cord, and multiple brain regions.

FIG. 16B schematically shows the results. CSF levels of methotrexate were analyzed over time. Drug levels were found to be very high in the lumbar region where the drug was infused and a decline over time was measured except for an increase at 5 hours and then a subsequent decline. CSF levels of methotrexate were very low in the ventricular samples initially, but with time, increased at 4 and 5 hours, before declining to a similar level as the lumbar samples.

FIG. 16C shows how samples from twelve regions of the brain were homogenized and analyzed for methotrexate levels and measured as ug/mL/g of tissue. The x-axis of this graph is drug levels. All areas of the brain and spinal cord had good levels of methotrexate. It will be appreciated that methotrexate that is administered typically subdural in the thigh typically does not cross the blood-brain barrier and would not be found in appreciable levels in brain and spinal cord as a result.

Example 2: Administration of Antisense Oligonucleotide to a Sheep Using Illustrative Embodiments The inventors administered an antisense oligonucleotide (ASO) for Huntington's disease to sheep using illustrative embodiments. An outline of the study is depicted in FIGS. 17A-C. Each sheep used for this experiment received the CSF circuit 10 of illustrative embodiments. Circulation was started at the same time that ASO was infused. ASO was infused at a rate of 2 mLs over 2 min. The dose of ASO infused was 30 mg. Circulation continued after drug infusion was stopped for four more hours. At zero to four hours, the circulation rate was at 0.2 mL/min. For unidirectional flow, the direction of the flow was lumbar to ventricle me for the entire 4 h. For the bidirectional flow, the first 1 h of flow was lumbar to ventricle, then the direction of flow was reversed to ventricle to lumbar for 10 min, then switched repeatedly for 10 min intervals for the remainder of the 4 h. All sheep in the study were necropsied after 48 h and tissues were collected to assay drug levels.

The assay for detection of the ASO is depicted in FIG. 17B. Sandwich hybridization ELISA (Enzyme-Linked-immuno-absorption-Assay) quantification used to measure the concentration of CAG repeats in tissue, CSF, and blood samples. Probes comprised of a sequence complementary to the analyte. Capture DNA probe conjugated to biotin label and applied to a streptavidin-coated microliter plate. Detection DNA probe with digoxigenin label was used. To detect digoxigenin label, anti-digoxigenin (anti-Dig) peroxidase (POD) is reacted with substrate TMB for the signal measurement by an absorption change with a plate reader.

FIG. 17C schematically shows the results. Samples from seventeen regions of the brain were homogenized and analyzed for ASO levels and measured as ug/g of tissue. The x-axis of this graph is drug levels. Most areas of the brain and spinal cord had good levels of ASO. It will be appreciated that the ASO if administered orally, subdurally, or intravenously typically does not cross the blood-brain barrier and would not be found in appreciable levels in brain and spinal cord as a result.

Of course, those skilled in the art should recognize that the above examples are two of many examples that may be used with illustrative embodiments.

Accordingly, illustrative embodiments enable a clinician to more effectively treat various diseases by targeting drug delivery via CSF in the subarachnoid space.

Various embodiments of the invention may be implemented at least in part in any conventional computer programming language. For example, some embodiments may be implemented in a procedural programming language (e.g., "C"), or in an object oriented programming language (e.g., "C++"). Other embodiments of the invention may be implemented as a pre-configured, stand-along hardware element and/or as preprogrammed hardware elements (e.g., application specific integrated circuits, FPGAs, and digital signal processors), or other related components.

In an alternative embodiment, the disclosed apparatus and methods (e.g., see the various flow charts described above) may be implemented as a computer program product for use with a computer system. Such implementation may include a series of computer instructions fixed either on a tangible, non-transitory medium, such as a computer readable medium (e.g., a diskette, CD-ROM, ROM, or fixed disk). The series of computer instructions can embody all or part of the functionality previously described herein with respect to the system.

Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

Among other ways, such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). In fact, some embodiments may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. Such variations and modifications are intended to be within the scope of the present invention as defined by any of the appended claims.

What is claimed is:

1. A CSF management system for use with a patient having a body with CSF having a natural flow rate, the system comprising:
   a CSF circuit configured to control flow of the CSF in the body;
   a therapeutic input fluidly coupled with the CSF circuit and configured to receive a bolus of therapeutic material into the CSF circuit;
   a pump configured to direct the therapeutic material, via the CSF circuit, toward a prescribed portion of the body; and
   a controller configured to vary the flow of the CSF in the CSF circuit to localize the CSF at the prescribed portion of the body, wherein varying comprises oscillating a direction of the CSF flow between opposing directions within the CSF circuit to maintain therapeutic material in the prescribed portion of the body.

2. The system as defined by claim 1 wherein localizing comprises oscillating the flow of the CSF within the CSF circuit for a prescribed time and at a prescribed frequency.

3. The system as defined by claim 1 wherein the therapeutic material comprises a drug.

4. The system as defined by claim 1 wherein the CSF circuit comprises a therapeutic delivery pump.

5. The system as defined by claim 1 wherein varying comprises flowing the CSF within the CSF circuit at two or more flow rates at two or more different times.

6. The system as defined by claim 1 wherein the CSF circuit comprises a closed loop channel configured to be in communication with a lower abdomen of a human being.

7. The system as defined by claim 1 wherein the CSF circuit is configured to access one or more CSF-containing compartments with patient anatomy, including one or more of lateral ventricles, a lumbar thecal sac, a third ventricle, a fourth ventricle, and a cisterna magna.

8. The system as defined by claim 1 wherein the CSF circuit is configured to produce pulsatile flow of the CSF.

9. The system as defined by claim 1 further comprising a mixing chamber configured to mix the therapeutic material and the CSF.

10. The system as defined by claim 1 further comprising a display to display a control panel interface configured to control one or both of CSF flow rate and an oscillation frequency.

11. The system as defined by claim 1 further comprising a therapeutic sensor configured to track the progression of the therapeutic material as the therapeutic material flows through the CSF circuit, further where the controller is configured to vary by reducing the CSF flow rate after the therapeutic material reaches the prescribed portion of the body.

12. The system as defined by claim 1 further comprising an imager configured to image the location of the CSF and/or the therapeutic material, the system configured to localize as a function of the location of the CSF and/or the therapeutic material.

13. The system as defined by 1 wherein the CSF circuit comprises a flow sensor, a pressure sensor, or both the flow sensor and the pressure sensor.

14. The system as defined by claim 13 wherein the CSF circuit comprises a catheter controller in communication with the pump, the catheter controller being configured to track a total number of uses of a fluid channel.

15. The system as defined by claim 14 wherein the CSF circuit comprises a catheter.

* * * * *